(12) United States Patent
Kurz et al.

(10) Patent No.: US 7,132,436 B2
(45) Date of Patent: Nov. 7, 2006

(54) INHIBITORS OF 11-β-HYDROXY STEROID DEHYDROGENASE TYPE 1

(75) Inventors: Guido Kurz, Stockholm (SE); Marianne Nilsson, Rimbo (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 10/296,552

(22) PCT Filed: May 22, 2001

(86) PCT No.: PCT/SE01/01158

§ 371 (c)(1), (2), (4) Date: Apr. 1, 2003

(87) PCT Pub. No.: WO01/90092

PCT Pub. Date: Nov. 29, 2001

(65) Prior Publication Data

US 2003/0166689 A1 Sep. 4, 2003

(30) Foreign Application Priority Data

May 22, 2000 (SE) .............................. 0001899

(51) Int. Cl.
*C07D 277/52* (2006.01)
*C07D 409/12* (2006.01)
*A61K 31/426* (2006.01)
*A61K 31/427* (2006.01)

(52) U.S. Cl. ............... 514/366; 514/370; 548/150; 548/151; 548/197

(58) Field of Classification Search ................ 548/150, 548/151, 197; 514/366, 370
See application file for complete search history.

(56) References Cited

U.S. PATENT DOCUMENTS

| | | | |
|---|---|---|---|
| 2,362,087 | A | 11/1944 | Newbery |
| 4,254,260 | A | 3/1981 | Takaya et al. |
| 5,403,857 | A | 4/1995 | Edwards et al. |
| 5,783,597 | A | 7/1998 | Beers et al. |
| 5,856,347 | A | 1/1999 | Hashiguchi et al. |
| 5,962,490 | A | 10/1999 | Chan et al. |
| 2003/0130258 | A1 | 7/2003 | Kurz et al. |
| 2003/0130279 | A1 | 7/2003 | Kurz et al. |
| 2003/0130318 | A1 | 7/2003 | Barf et al. |
| 2003/0176476 | A1 | 9/2003 | Barf et al. |
| 2003/0199501 | A1 | 10/2003 | Nilsson et al. |

FOREIGN PATENT DOCUMENTS

| | | |
|---|---|---|
| EP | 0 749 964 A1 | 12/1996 |
| EP | 0 790 057 A1 | 8/1997 |
| EP | 0 819 681 A2 | 1/1998 |
| EP | 1 069 114 A2 | 1/2001 |
| FR | 94.123 | 5/1969 |
| FR | 2 384 498 A1 | 10/1978 |
| GB | 620654 | 7/1940 |
| GB | 822947 | 11/1959 |
| GB | 6610324 | 1/1969 |
| JP | 03173876 A2 | 7/1991 |
| JP | 687841 A | 3/1994 |
| NL | 6610324 | 1/1967 |
| WO | WO 96/04912 A1 | 2/1996 |
| WO | WO 97/07789 A1 | 3/1997 |
| WO | WO 98/16520 | 4/1998 |
| WO | WO 98/27081 | 6/1998 |
| WO | WO 98/36770 A1 | 8/1998 |
| WO | WO 99/02502 | 1/1999 |
| WO | WO 99/28306 A1 | 6/1999 |
| WO | WO 99/65884 | 12/1999 |
| WO | WO 00/02851 A1 | 1/2000 |
| WO | WO 01/01971 A1 | 1/2001 |
| WO | WO 01/52833 A1 | 7/2001 |
| WO | WO 01/54691 A1 | 8/2001 |
| WO | WO 01/90090 A1 | 11/2001 |
| WO | WO 01/90091 A1 | 11/2001 |
| WO | WO 02/28353 A2 | 4/2002 |
| WO | WO 03/011258 A1 | 2/2003 |

OTHER PUBLICATIONS

Rover et al., J. Med. Chem., (1997), 40, 4378–4385.*
CAPLUS, "2–Thiophenecarboxamide, N–(2, 6–dimethylphenyl)–3–((phenylsulfonyl)amino)–(9CI)," Caplus Registry No. 409362–72–7.
CAPLUS, "2–Thiophenecarboxamide, N–butyl–3–(phenylsulfonyl)amino)–((CI)," Caplus Registry No. 409362–91–0.
CAPLUS, "2–Thiophenecarboxamide, N–(2–methylphenyl)–3–((phenylsulfonyl)amino)–9CI)," Caplus Registry No. 409363–32–2.
Hökfelt, Bernt, "Hypoglycemic Activity in Relation to Chemical Structure of Potential Oral Antidiabetic Substances. I. 1–Sulfonyl–3–alkylureas", *Journal of Medicinal and Pharmaceutical Chemistry*, 5(1):231–257, Jan. 6, 1962.
Sonino et al., "Ketoconazole treatment in Cushing's Syndrome: Experience in 34 Patients", *Clinical Endrocrinology*, 35:347–352 (1991).
Verhelst et al., "Use of ketoconazole in the treatment of a virilizing adrenocortical carcinoma", *Acta Endrocrinologica*, 121:229–234 (1989).
Hisamitsu Pharmaceutical Co: "Preparation of 2–(substituted amino)thiazole derivatives as esterase inhibitors," CAPLUS Accession No. 1995:818696, Document No. 123:228174 (1995).
Hisamitsu Pharmaceutical Co: "Preparation of 2–aminothiazole derivatives as esterase inhibitors," CAPLUS Accession No. 1995:867676, Document No. 123:256699 (1995).

(Continued)

*Primary Examiner*—Kamal A. Saeed
*Assistant Examiner*—Rebecca Anderson
(74) *Attorney, Agent, or Firm*—Foley & Lardner LLP

(57) ABSTRACT

The present invention relates to compounds with the formula (I) and also to pharmaceutical compositions comprising the compounds, to processes for their preparation, as well as to the use of the compounds in medicine and for the preparation of a medicament which acts on the human 11-β-hydroxysteroid dehydrogenase type 1 enzyme.

10 Claims, No Drawings

OTHER PUBLICATIONS

Susan Budavari et al., "The Merck Index, An Encyclopedia of Chemical, Drugs, and Biologicals, Twelfth Edition," No. 9115, pp. 1529 (1996).

Friedrich Boberg et al., "Reaction of thioxo compounds with N–chloramidines. VI. Reaction of thioquinolone, dihydrothiazolethione and dihydroisothiazole thione with sodium N–chlorobenzenesulfonamides," CAPLUS Accession No. 1996:420288, Document No. 125:195596 (1996).

CHEMCATS Accession No. 1998:584450, Maybridge 2000–04–03, (1998).

CHEMCATS Accession No. 1998:584451, Maybridge, 2000–04–03 (1998).

Hisamitsu Pharmaceutical Co: "Preparation of 2–(substituted amino)thiazole derivatives as esterase inhibitors," CAPLUS Accession No. 1995:818696, Document No. 123:228174 (1995).

Asahi Chemical Ind: "Therapeutics for Alzheimer's disease containing N–(5–nitro–2–thiazolyl)benzenesulfonamides," CAPLUS Accession No. 1996:111694, Document No. 124:165271 (1996).

Hisamitsu Pharmaceutical Co: "Preparation of diphenylthiazoles as pharmaceuticals," CAPLUS Accession No. 1991:680016, Document No. 115:280016, (1991).

Zaki El–Hewehi et al., "Sulfonic acid derivatives: preparation and applicability as mothproofing agents," Chemical Abstracts, vol. 58, The Abstract No. 5671, J. Prakt. Chem., pp. 297–336 (1962).

AsInEx Compound Collection, "5–Thiazolecarboxylic acid, 4–methyl–2–(((4–methylphenyl)sulfonyl)amino)–, ethyl ester," CHEMCATS Accession No. 2001:67657, (2001).

Pharma Library Collection, "5–Thiazolecarboxylic acid, 2–(((4–chlorophenyl)sulfonyl)amino)–4–methyl–, ethyl ester," CHEMCATS Accession No. 2001:19109, (2001).

ChemDiv, Inc. Product Library, Apr. 26, 2001, "5–Thiazolecarboxylic acid, 4–methyl–2–(((4–methylphenyl)sulfonyl)amino–), ethyl ester," CHEMCATS Accession No. 2001:444469, (2001).

V.V. Berezhinskaya, "hypoglycemic activity in relation to chem. Structure of potential oral antidiabetic substances— (I) 1–sulfonyl–3–alkylures, (II) analogs of 1–sulfonyl–3–alkylureas, (III) 2–benzene–sulfonamido–5–alkyl–1,3,4–thiadiazole and–oxadiazoles," CA OLD Accession No. CA57:3567g (1962).

Hans Wojahn, "Bromination of sulfapyrimidine and sulfathiazole compounds. II.," Chemical Abstracts, vol. 51, The Abstract No. 6646d, Arch. Pharm. pp. 288, 321–336 (1955).

V.A. Krasovskii et al., "Alkylation of aminothiazoles. VII. Alkylation of 2–aminothiazole and 4–methyl–2–aminothiazole by tert–butyl alcohol," CAPLUS accession No. 1969:115051, Document No. 70:115051, (1969).

J.D. McColl et al., "Effect of Some Sulfonylurea Derivatives in Experimental Ulcer Formation in the Rat," Chemical Abstracts, vol. 59, The Abstract No. 3231, Arch. Intern. Pharmacodyn, pp. 181–189 (1963).

Gaile E. Gudriniece et al., "Heterocyclic compounds based on diketones. II. 2'–Amino–5, 5–dimethyl–1–cyclohexanone(2,3:4', 5')thiazole. I.," Chemical Abstracts, vol. 59, The Abstract No. 6380 (1962).

Anton–Fos et al., "Pharmacological Studies of the Two New Hypoglycaemic Compounds 4–(3–Methyl–5–oxo–2–pyrazolin–1–yl)benzoic Acid and 1–(Mesitylen–2–sulfonyl)–1H–1,2,4–triazole," Arzneim.–Forsch./Drug Res 44(11), No. 7, 1994, pp. 821–826.

Merck & Co. Inc., USA, 1999, Monograph No. 4488, "Glybuzole," CAS Registry No. 1492–02–0.

Merck & Co. Inc., USA, 1999, Monograph No. 9084, "Sulfamethizole," CAS Registry No. 144–82–1.

CAPLUS, "2–Thiophenecarboxamide, N–2–naphthalenyl–3–((phenylsulfonyl)amino)–(9CU)", Caplus Registry No. 409362–65–8. (Supplement to Reference AS), 2002.

CAPLUS, "Thiophenecarboxamide, N–1–naphthalenyl–3–((phenylsulfonyl)amino)–(9CI)," Caplus Registry No. 409363–57–1. (Supplement to Reference AS), 2002.

CAPLUS, "2–Thiophenecarboxamide, 3–((phenylsulfonyl)amino)–N–(3–thienylmethyl)–(9CI)," Caplus Registry No. 409363–56–0. (Supplement to Referency AY), 1969.

CAPLUS, "2–Thiophenecarboxamide, 3–((phenylsulfonyl)amino)–N–(2–thienylmethyl)–(9CI),", Caplus Registry No. 409362–88–5. (Supplement to Reference AS), 2002.

CAPLUS, "2–Thiophenecarboxamide, N–(2–phenylethyl)–3–((phenylsulfonyl)amino)–(9CI),", Caplus Registry No. 409362–99–8. (Supplement to Reference AS), 2002.

CAPLUS, "2–Thiophenecarboxamide, N–(2, 3–dimethylphenyl)–3–((phenylsulfonyl)amino)–(9CI)," Caplus Registry No. 409362–97–6. (Supplement to Reference AY), 1969.

CAPLUS, "2–Thiophenecarboxamide, N–(4–ethylphenyl)–3–((phenylsulfonyl)amino)–(9CI)," Caplus Registry No. 409362–93–2. (Supplement to Reference AS), 2002.

CAPLUS, "2–Thiophenecarboxamide, N–(2, 6–dimethylphenyl)–3–((phenylsulfonyl)amino)–(9CI)," Caplus Registry No. 409362–72–7. (Supplement to Reference AS), 2002.

CAPLUS, "2–Thiophenecarboxamide, N–butyl–3–((phenylsulfonyl(amino)–(9CI)," Caplus Registry No. 409362–91–0. (Supplement to Reference AS), 2002.

CAPLUS, "2–Thiophenecarboxamide, N–(2–methoxyethyl)–3–((phenylsulfonyl)amino)–(9CI)," Caplus Registry No. 409363–48–0. (Supplement to Reference AS), 2002.

CAPLUS, "2–Thiophenecarboxamide, N–(2–methylphenyl)–3–((phenylsulfonyl)amino)–(9CI)," Caplus Registry No. 409363–32–2. (Supplement to Reference AS), 2002.

CAPLUS, "2–Thiophenecarboxamide, N–(phenylmethyl)–3–((phenylsulfonyl)amino))–(9CI)," Caplus Registry No. 409362–89–6. (Supplement to Reference AS), 2002.

CAPLUS, "Benzenesulfonamide, 4–methoxy–N–(2–((1E)–2–(4–pyridinyl)ethenyl)–3–thienyl)–(9CI)," Caplus Registry No. 362629–53–6. (Supplement to Reference AS), 2002.

CAPLUS, "2–Thiophenecarboxamide, N–(1, 1–dimethylpropyl)–3–((phenylsulfonyl)amino)–(9CI)," Caplus Registry No. 409363–45–7. (Supplement to Reference AS), 2002.

CAPLUS, "2–Thiophenecarboxamide, N–(2–furanylmethyl)–3–((phenylsulfonyl)amino)–(9CI)," Caplus Registry No. 409363–44–6. (Supplement to Reference AS), 2002.

CAPLUS, 2–Thiophenecarboxamide, N–(4–(1–methylethyl)phenyl)–3–((phenylsulfonyl)amino)–(9CI), Caplus Registry No. 409362–29–4. (Supplement to Reference AS), 2002.

Kim, C.H et al., J. Endocrinol, vol. 162, pp. 371–379 (1999).

C.G. Bellows et al., Bone, vol. 23, pp. 119–125 (1998).

M.S. Cooper et al., Bone, vol. 27, pp. 375–381 (2000).

Analgesic tetrahydrothiazolo[5,4–c]pyridines, Fr. Addn., Addn to FR. 1498465, (1969).

* cited by examiner

INHIBITORS OF 11-β-HYDROXY STEROID DEHYDROGENASE TYPE 1

CROSS REFERENCE TO RELATED APPLICATIONS

The present application is a national phase application under 35 U.S.C. Section 371 filed from International Patent Application PCT/SE0/01158, filed 22 May 2001, which claims priority to Swedish patent application Ser. No. 0001899-4, filed 22 May 2000. The contents of these applications are incorporated herein by reference in their entirety.

TECHNICAL FIELD

The present invention relates to novel compounds, to phamaceutical compositions comprising the compounds, to processes for their preparation, as well as to the use of the compounds in medicine and for the preparation of a medicament which acs on the human 11-β-hydroxysteroid dehydrogenase type 1 enzyme (11βHSD1).

BACKGROUND ART

1. Glucorticoids, Diabetes and Hepatic Glucose Production

It has been known for more Dan half a century that glucocorticoids have a central role in diabetes, e.g. the removal of the pituitary or the adrenal gland from a diabetic animal alleviates the most severe symptoms of diabetes and lowers the concentration of glucose in the blood (Long, C.D. and F.D.W. Leulis (1936) J. Exp. Med. 63:465–490; Houssay, B.A. (1942) Endocrinology 30: 884–892). It is also well established that glucocorticoids enable the effect of glucagon on the liver.

The role of 11βHSDL as an important regulator of local glucocorticoid effect and thus of hepatic glucose production is well substantiated (see e.g. Jamieson et al. (2000) J. Endocrinol. 165: p. 685–692). The hepatic insulin sensitivity was improved in healthy human volunteers treated with the non-specific 11βHSD1 inhibitor carbenoxolone (Walker, B.R. et al. (1995) J. Clin. EndocrinoL Metab. 80: 3155–3159). Furthennore, the expected mechanism has been established by different experiments with mice and rats. These studies showed that the MRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6Pase) catalyzing the last common step of gluconeogenesis and glycogenolysis. Finally, the blood glucose level and hepatic glucose production is reduced in mice having the 11βHSD1 gene knocked-out. Data from this model also confirm that inhibition of 11βHSD1 will not cause hypoglycemia, as predicted since the basal levels of PEPCK and G6Pase are regulated independently of glucocorticoids (Kotelevtsev, Y. et al., (1997) Proc. Natl. Acad. Sci. USA 94: 14924–14929).

2. Possible Reduction of Obesity and Obesity Related Cardiovascular Risk Factors Obesity is an important factor in syndrome X as well as in the majority (>80%) of type 2 diabetic, and omental fat appears to be of central importance. Abdominal obesity is closely associated with glucose intolerance, hyperinsulinemia, hypertriglyceridemia, and other factors of the so-called syndrome X (e.g. raised blood pressure, deceased levels of HDL and increased levels of VLDL) (Montague & O'Rahilly, Diabetes 49: 883–888, 2000). Inhibition of the enzyme in pre-adipocytes (stromal cells) has been shown to decrease the rate of differentiation into adipocytes. This is predicted to result in diminished expansion (possibly reduction) of the omental fat depot, i.e. reduced central obesity (Bujalska, I. J., S. Kumar, and P. M. Stewart (1997) Lancet 349: 1210–1213).

Inhibition of 11βHSD1 in mature adipocytes is expected to attenuate secion of the plasminogen activator inhibitor 1 (PAI-1)—an independent cardiovascular risk factor (Halleux, C. M. et al. (1999) J. Clin. Endocrinol. Metab. 84: 4097–4105). Furthermore, there is a clear correlation between glucocorticoid "activity" and cardiovascular risk factore suggesting that a reduction of the glucocorticoid effects would be beneficial (Walker, B. R. et al. (1998) Hypertension 31: 891–895; Fraser, R. et al. (1999) Hypertension 33: 1364–1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 137814 1383).

3. Possible Beneficial Effect on the Pancreas

Inhibition of 11βHSD1 in isolated murine pancreatic β-cells improves the glucose-stimulated insulin secretion (Davani, B. et al. (2000) J. Biol. Chem. 2000 Nov 10; 275(45): 34841-4). Glucocorticoids were previously known to reduce pancreatic insulin release in vivo (Billaudel, B. and B. C. J. Sutter (1979) Horm. Metab. Res. 11: 555–560). Thus, inhibition of 11βHSD1 is predicted to yield other beneficial effects for diabetes treatment, besides effects on liver and fat.

4. Possible Beneficial Effects on Cognition and Dementia

Stress and glucocorticoids influence cognitive function (de Quervain, D. J. -F., B. Roozendaal, and J. L. McGaugh (1998) Nature 394: 787–790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65–70; Seckl, J. R., Front. (2000) Neuroendocrinol. 18: 49–99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99–103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite (previous section).

5. Possible Use of Immuno-Modulation using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillier's Clin. Endocrinol. Metab. 13: 576–581). The balance between the cell-mediated response and humoral responses is modulated by glucocorticoids. A high glucocorticoid activity, such as at a state of stress, is associated with a humoral response. Thus, inhibtion of the enzyme 11βHSD1 has been suggested as a means of shifting the response towards a cell-based reaction.

In certain disease states, including tuberculosis, lepra and psoriasis the immune reaction is normally biased towards a humoral response when in fact the appropriate response would be cell based. Temporal inhibition of 11βHSD1, local or systemic, might be used to push the imme system into the appropriate response (Mason, D. (1991) Immunology Today 12: 57–60; Rook et al., supra).

An analogous use of 11βHSD1 inhibition, in this case temporal, would be to booster the immune response in association with immunization to ensure that a cell based response would be obtained, when desired.

6. Reduction of Intraocular Pressure

Recent data suggest that the levels of the glucocorticoid target receptors and the 11βHSD enzymes determines the susceptibility to glaucoma (Stokes, J. et al. (2000) Invest. Ophthalmol. 41: 1629–1638). Further, inhibition of 11βHSD1 was recently presented as a novel approach to lower the intraocular pressure (Walker E. A. et al, poster P3-698 at the Endocrine society meeting June 12–15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithelialium of the cornea (the site of aqueous production), to ciliary muscle and to the sphincter and dilator muscles of the iris. In contrast, the distant isoenyzme 11βHSD2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., S. L. Cheng, and G. S. Kim (1999) J. Endocrinol. 162: 371–379). The negative effect on bone nodule formation could be blocked by the non-specific inhibitor carbenoxolone suggesting an important role of 11βHSD1 in the glucocorticoid effect (Bellows, C. G., A. Ciaccia, and J. N. M. Heersche, (1998) Bone 23: 119–125). Other data suggest a role of 11βHSD1 in providing sufficiently high levels of active glucocorticoid in osteoclasts, and thus in augmenting bone resorption (Cooper, M. S. et al. (2000) Bone 27: 375–381). Taken together, these different data suggest that inhibition of 11βHSD1 may have beneficial effects against osteoporosis by more than one mechanism working in parallel.

WO 99/65884 discloses carbon subtituted aminothiazole inhibitors of cyclin dependent kinases. These compounds may e.g. be used against cancer, inflammation and arthritis. U.S. Pat. No. 5,856,347 discloses an antibacterial preparation or bactericide cmprising 2-aminothiazole derivative and/or salt thereof. Further, U.S. Pat. No. 5,403,857 discloses benzenesulfonamide derivatives having 5-lipoxygenase inhibitory activity. Additionaly, tetrahydrothiazolo[5,4-c]pyridines are disclosed in: Analgesic tetrahydrothiazolo[5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968: 49593 CAPLUS.

FR 2384498 discloses thiazolo-benzenesulfonamides which show antibacterial, antifungal and hypoglycaemic properties. WO99/28306 and EP 0 819 681 A2 relate to thiazolobenzenesulfonamides which can be used for treating neurodegenerative pathologies, such as Alzheimer's disease. JP 7149745 A2 and JP 7149746 A2 both describe 2-aminothiazole derivatives as esterase inhibitors. Nothing is disclosed about inhibiting 11βHSD1. JP 7309757 A2 relates to treating Alzheimer's disease using N-(5-nitro-2-thiazolyl)benzenesulfonamides. JP 3173876 A2 presents preparation of diphenylthiazoles. These compounds are used as anti-inflammatories, analgesics, anti-allergy agents, uric acid accelerators and blood platelet aggregation inhibitors. EP 0 790 057 A1 discloses an antibacterial or bactericide comprising a 2-aminothiazole derivative. U.S. Pat. No. 2 362 087 describes the preparation of thiazolobenzenesulfonamides, such as 2-bromobenzenesulfonamido-4-methylthiazole. Nothing is disclosed about inhibiting 11βHSD1 and no thrapeutic use of such substances is disclosed.

However, none of the above disclosures discloses the compounds according to the present invention, or their use for the treatment of diabetes, obesity, glaucoma, osteoporosis, cognitive disorders, immune disorders, and depression.

Consequently, there is a need of new compounds that are useful in the treatment of diabetes, obesity, glaucoma, osteoporosis, cognitive disorders, immune disorders, and depression.

DISCLOSURE OF THE INVENTION

The compounds according to the present invention solve the above problems and embraces a novel class of compounds which has been developed and which inhibit the human 11β-hydroxysteroid dehydrogenase type 1 enzyme (11-β-$HSD_1$), and may therefore be of use in the treating disorders such as diabetes, obesity, glaucoma, osteoporosis, cognitive disorders; immune disorders, and depression.

One object of the present invention is A compound of the formula (I):

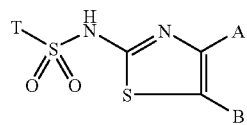

wherein
T is selected from thienyl substituted with one or more of bromo, chloro;
phenyl substituted as follows:
  a) either T is phenyl, wherein the phenyl is substituted with one or more of propyl and phenyl;
  b) T is phenyl substituted with chloro in position 3 and methyl in position 2;
  c) T is phenyl substituted with chloro in position 2 and 4, and methyl in position 6;

d) T is phenyl substituted with bromo in position 4 and fluoro in position 2 and 5;
e) T is phenyl substituted with chloro in position 2, 3, and 4;
f) T is phenyl substituted with chloro in position 2, 4, and 5;
g) T is phenyl substituted with bromo in position 4 and methyl in position 2;
h) T is phenyl substituted with chloro in position 2 and 6;
i) T is phenyl substituted with chloro in position 2, 4, and 6; or
j) T is phenyl substituted with bromo in position 4 and chloro in position 5.

A is selected from an aryl ring or heteroaryl ring, which can further be optionally substituted in one or more positions independently of each other by hydrogen, $C_{1-6}$-alkyl, halogenated $C_{1-6}$-alkyl, halogen, $C_{1-6}$-alkoxy, nitro, $C_{1-6}$-alkoxycarbonyl, $C_{1-6}$-alkylsulfonyl, acetylamino or aryloxy, wherein the aryloxy can further be optionally substituted in one or more positions independently of each other by hydrogen and halogen;

B is selected from hydrogen and $C_{1-6}$-alkoxycarbonyl or is linked to A to give a 6-membered aromatic or non-aromatic ring;

as well as pharmaceutically acceptable salts, hydrates and solvates thereof.

It is preferred that:

A is selected from 1-benzothien-3-yl, 3-(2,5-dimethylfuryl), pyridinyl;

thienyl optionally substituted with one or more of chloro, methylsulfonyl;

phenyl optionally substituted with one or more of ethoxycarbonyl, nitro, fluoro, methyl, methoxy, acetylamino, chloro, 4-chlorophenoxy, trifluoromethyl;

B is selected from hydrogen, carbethoxy or is linked to A to give a 6-membered aromatic or non-aromatic ring.

Specific examples of compounds according to the present invention are:

Ethyl 2-{[(3-chloro-2-methylphenyl)sulfonyl]amino}-4-phenyl-1,3-thiazole-5-carboxylate,
N-[4-(3-nitrophenyl)-1,3-thiazol-2-yl]-4-propylbenzenesulfonamide,
N-[4-phenyl-1,3-thiazol-2-yl]4-propylbenzenesulfonamide,
N-[4-(4-fluoro-3-methylphenyl)-1,3-thiazol-2-yl]-4-propylbenzenesulfonamide,
N-[4-(4-methoxyphenyl)-1,3-thiazol-2-yl]-4-propylbenzenesulfonamide,
3-Chloro-2-methyl-N-[4-(3-nitrophenyl)-1,3-thiazol-2-yl]benzenesulfonamide,
3-Chloro-2-methyl-N-(4-phenyl-1,3-thiazol-2-yl)benzenesulfonamide,
3-Chloro-N-[4-(4-fluoro-3-methylphenyl)-1,3-thiazol-2-yl]-2-methylbenzenesulfonamide,
2,4,6-Trichloro-N-[4-(3-nitrophenyl)-1,3-thiazol-2-yl]benzenesulfonamide,
2,4,6-Trichloro-N-(4-phenyl-1,3-thiazol-2-yl)benzenesulfonamide,
2,4,6-Trichloro-N-[4-(4-fluoro-3-methylphenyl)-1,3-thiazol-2-yl]benzenesulfonamide,
2,4,6-Trichloro-N-[4-(4-methoxyphenyl)-1,3-thiazol-2-yl]benzenesulfonamide,
N-[4-(3-nitrophenyl)-1,3-thiazol-2-yl][1, 1'-biphenyl]-4-sulfonamide,
N-(4-phenyl-1,3-thiazol-2-yl)[1, 1'-biphenyl]-4-sulfonamide,
N-[4-(4-Fluoro-3-methylphenyl)-1,3-thiazol-2-yl][1,1'-biphenyl]-4-sulfonamide,
N-[4-(4-Methoxyphenyl)-1,3-thiazol-2-yl][1,1'-biphenyl]-4-sulfonamide,
2,4-Dichloro-6-methyl-N-[4-(3-nitrophenyl)-1,3-thiazol-2-yl]bezenesulfonamide,
2,4-Dichloro-6-methyl-N-(4-phenyl-1,3-thiazol-2-yl)benzenesulfonamide,
2,4-Dichloro-N-[4-(4-fluoro-3-methylphenyl)-1,3-thiazol-2-yl]-6-methylbenzenesulfonamide,
2,4-Dichloro-N-[4-(4-methoxyphenyl)-1,3-thiazol-2-yl]-6-methylbenzenesulfonamide,
N-[4-(2-{[(4-propylphenyl)sulfonyl]amino}-1,3-thiazol-4-yl)phenyl]acetamide,
4-Propyl-N-[4-(3-pyridinyl)-1,3-thiazol-2-yl]benzenesulfonamide,
N-[4-(2-chloro-5-nitrophenyl)-1,3-thiazol-2-yl]-4-propylbenzenesulfonamide,
N-(7-methoxy4,5-dihydronaphtho[1,2-d][1,3]thiazol-2-yl)4-propylbenzenesulfonamide,
N-[4-(5-chloro-2-thienyl)-1,3-thiazol-2-yl]-4-propylbenzenesulfonamide,
N-[4-(2-chlorophenyl)-1,3-thiazol-2-yl]-4-propylbenzenesulfonamide,
N-[4-(2-{[(3-chloro-2-methylphenyl)sulfonyl]amino}-1,3-thiazol-4-yl)phenyl]acetamide,
3-Chloro-2-methyl-N-[4-(3-pyridinyl)-1,3-thiazol-2-yl]benzenesulfonamide,
3-Chloro-N-[4-(2-chloro-5-nitrophenyl)-1,3-thiazol-2-yl]-2-methylbenzenesulfonamide,
3-Chloro-N-(7-methoxy-4,5-dihydronaphtho[1,2-d][1,3]thiazol-2-yl)-2-methylbenzenesulfonamide,
3-Chloro-N-[4-(5-chloro-2-thienyl)-1,3-thiazol-2-yl]-2-methylbenzenesulfonamide,
3-Chloro-N-[4-(2-chlorophenyl)-1,3-thiazol-2-yl]-2-methylbenzenesulfonamide,
N-[4-{[(2,4,6-trichlorophenyl)sulfonyl]amino}-1,3-thiazol-4-yl)phenyl]acetamide,
2,4,6-Trichloro-N-[4-(3-pyridinyl)-1,3-thiazol-2-yl]benzenesulfonamide,
2,4,6-Trichloro-N-[4-(2-chloro-5-nitrophenyl)-1,3-thiazol-2-yl]benzenesulfonamide,
2,4,6-Tricbloro-N-(7-methoxy-4,5-dihydronaphtho[1,2-d][1,3]thiazol-2-yl)benzenesulfonamide,
2,4,6-Trichloro-N-[4-(5-chloro-2-thienyl)-1,3-thiazol-2-yl]benzenesulfonamide,
2,4,6-Trichloro-N-[4-(2-chlorophenyl)-1,3-thiazol-2-yl]benzenesulfonamide,
N-(4-{2-[([1, 1'-biphenyl]-ylsulfonyl)amino]-1,3-thiazol-4-yl}phenyl)acetamide,
N-[4-(3-pyridinyl)-1,3 -thiazol-2-yl][1,1'-biphenyl]-4-sulfonamide,
N-[4-(2-chloro-5-nitrophenyl)-1,3thiazol-2-yl][1,1'-biphenyl]-4-sulfonamide,
N-(7-methoxy-4,5-dihydroaphtho[1,2-d][1,3]thiazol-2-yl)[1,1'-biphenyl]-4-sulfonamide,
N-[4-(5-chloro-2-thienyl)-1,3-thiazol-2-yl][1,1'-biphenyl]-4-sulfonamide,
N-[4-(2-chlorophenyl)-1,3-thiazol-2-yl][1,1'-biphenyl]-4-sulfonamide,
N-[4-(2-{[(2,4-dichloro-6-methylphenyl)sulfonyl]amino}-1,3-thiazol-4-yl)phenyl]acetamide,
2,4-Dichloro-6-methyl-N-[4-(3-pyridinyl)-1,3-thiazol-2-yl]benzenesulfonamide,
2,4-Dichloro-N-[4-(2-chloro-5-nitrophenyl)-1,3-thiazol-2-yl]-6-methylbenzenesulfonamide,
2,4-Dichloro-N-(7-methoxy-4,5-dihydronaphtho[1,2-d][1,3]thiazol-2-yl)-6-methylbenzenesulfonamide,
2,4-Dichloro-N-[4-(5-chloro-2-thienyl)-1,3-thiazol-2-yl]-6-methylbenzenesulfonamide, 2,4-Dichloro-N-[4-(2,5-dimethyl-3-furyl)-1,3-thiazol-2-yl]-6-methylbenzenesulfonamide,
N-[4-(1-benzothien-3-yl)-1,3-thiazol-2-yl]-2,4-dichloro-6-methylbenzenesulfonamide,
N-[4-(3-chloro-2-thienyl)-1,3-thiazol-2-yl]-4-propylbenzenesulfonamide,
3-Chloro-N-[4-(3-chloro-2-thienyl)-1,3-thiazol-2-yl]-2-methylbenzenesulfonamide,
2,4,6-Trichloro-N-[4-(3-chloro-2-thienyl)-1,3-thiazol-2-yl]benzenesulfonamide,
2,4-Dichloro-N-[4-(3-chloro-2-thienyl)-1,3-thiazol-2-yl]-6-methylbenzenesulfonamide,
2,4-Dichloro-N-[4-(2-chlorophenyl)-1,3-thiazol-2-yl]-6-methylbenzenesulfonamide,
Ethyl 2-[{([1,1'-biphenyl]-4-ylsulfonyl)amino]-4-phenyl-1,3-thiazole-5-carboxylate,
3-Chloro-N-[4-(4-methoxyphenyl)-1,3-thiazol-2-yl]-2-methylbenzenesulfonamide,
N-[4-(2-{[(4-Bromo-2,5-difluorophenyl)sulfonyl]amino}-1,3-thiazol-4-yl)phenyl]acetamide,
2,3,4-Trichloro-N-[4-(2-chlorophenyl)- 1,3-thiazol-2-yl]benzenesulfonamide,
2,4,5-Trichloro-N-[4-(3-chloro-2-thienyl)-1,3-thiazol-2-yl]benzenesulfonamide,
2,3,4-Trichloro-N-[4-(3-chloro-2-thienyl)-1,3-thiazol-2-yl]benzenesulfonamide,
4-Bromo-N-[4-(3-chloro-2-thienyl)-1,3-thiazol-2-yl]-2,5-difluorobenzenesulfonamide,
4,5-Dichloro-N-(7-methoxy-4,5-diydronaphto[1,2-d][1,3]thiazol-2-yl)-2-thiophenesulfonamide,
4,5-Dichloro-N-[4-(2-chlorophenyl)-1,3-thiazol-2-yl]-2-thiophenesulfonamide,
N-[4-(2-{[(2,4,5-Trichlorophenyl)sulfonyl]amino}-1,3-thiazol-4-yl)phenyl]acetamde,
2,3,4-Trichloro-N-(7-methoxy-4,5-dihydronaphtho[1,2-d][1,3]thiazol-2-yl)benzenesulfonamide,
4-Bromo-5-chloro-N-[4-(3-chloro-2-thienyl)-1,3-thiazol-2-yl]-2-thiophenesulfonamide,
3-Bromo-5-chloro-N-(7-methoxy-4,5-dihydronaphtol[1,2-d][1,3]thiazol-2-yl)-2-thiophenesulfonamide,
3-Bromo-5-chloro-N-[4-(2-chlorophenyl)-1,3-thiazol-2-yl]-2-thiophenesulfonamide,
N-[4-(2-{[(2,6-Dichlorophenyl)sulfonyl]amino}-1,3-thiazo4-yl)phenyl]acetamide,
2,6-Dichloro-N-[4-(3-chloro-2-thienyl)-1,3-thiazol-2-yl]benzenesulfonamide,
2,4,6-Trichloro-N-(7,8-dimethoxy-4,5-dihydronaphtho[1,2-d][1,3]thiazol-2-yl)benzenesulfonamide,
2,3,4-Trichloro-N-{4-[2-chloro-4-(4-chlorophenoxy)phenyl]-1,3-thiazol-2-yl}benzenesulfonamide,
2,3,4-Trichloro-N-{4-[2,6-dichloro-4-trifluoromethyl)phenyl]-1,3-thiazol-2-yl}benzenesulfonamide,
N-[4-(2-Chloro-6-fluorophenyl)-1,3-thiazol-2-yl]-4-propylbenzenesulfonamide,
4-Bromo-N-{4-[2-chloro-4-(4-chlorophenoxy)phenyl]-1,3-thiazol-2-yl}-2,5-difluorobenzenesulfonamide,
4-Bromo-N-{4-[2,6-dichloro-4-(trifluoromethyl)phenyl]-1,3-thiazol-2-yl}-2,5-difluorobenzenesulfonamide,
4,5-Dichloro-N-[4-(2-chloro-6-fluorophenyl)-1,3-thiazol-2-yl]-2-thiophenesulfonamide,
4-Bromo-5-chloro-N-{4-[2-chlorophenoxy)phenyl]-1,3-thiazol-2-yl}-2-thiophenesulfonamide,
4-Bromo-5-chloro-N-{4-[2,6-dichloro-4-(trifluoromethyl)phenyl]-1,3-thiazol-2-yl}-2-thiophenesulfonamide,
2,4-Dichloro-N-[4-(2-chloro-6-fluorophenyl)-1,3-thizol-2-yl]-6-methylbenzenesulfonamide,
2,4,6-Trichloro-N-{4-[2,6-dichloro-4-(trifluoromethyl)phenyl-1,3-thiazol-2-yl}benznesulfonamide,
4-Bromo-N-[4-(2-chloro-6-fluorophenyl)-1,3-thiazol-2-yl]-2-methylbenzenesulfonamide,
2,4,6-riTchloro-N-{4-[2-chloro-4-(4-chlorophenoxy)phenyl]-1,3-thiazol-2-yl}benzenesulfonamide,
N-[4-(2-{[(4-Bromo-5-chloro-2-thienyl)sulfonyl]amino}-1,3-thiazol-4-yl)phenyl]acetamide,
3-Chloro-N-(4,5-dihydrothieno[3,2-e][1,3]benzothiazol-2-yl)-2-methylbenzenesulfonamide,
2,4,6-Trichloro-N-(4,5-dihydrothieno[3,2-e][1,3]benzothiazol-2-yl)benzenesulfonamide,
N-(4,5-Dihydrothieno[3,2-e][1,3]benzothiazol-2-yl)[1,1'-biphenyl]-4-sulfonamide,
2,4-Dichloro-N-(4,5-dihydrothieno[3,2-e][1,3]benzothiazol-2-yl)-6-methylbenzenesulfonamide,
N-(4,5-Dihydrothieno[3,2-e][1,3]benzothiazol-2-yl)-4-propylbenzenesulfonamide,
3-Chloro-N-[6-chloro-8-(methylsulfonyl)-4,5-dihydrothieno[3,4-e][1,3]benzothiazol-2-yl]-2-methylbenzenesulfonamide,
N-[6-Chloro-8-(methylsulfonyl)-4,5-dihydrothieno[3,4-e][1,3]benzothiazol-2-yl]-4-propylbenzenesulfonamide,
2,4-Dichloro-N-[6-chloro-8-(methylsulfonyl)-4,5-dihydrothieno[3,4-e][1,3]benzothiazol-2-yl]-6-methylbenzenesulfonamide,
N-[6-Chloro-8-(methylsulfonyl)-4,5-dihydrothieno[3,4-e][1,3]benzothiazol-2-yl][1,1'-biphenyl]-4-sulfonamide,
N-(2-{[(3-Chloro-2-methylphenyl)sulfonyl]amino}naphthol[1,2-d][1,3]thiazol-6-yl)acetamide,
N-(2-{[(4-Propylphenyl)sulfonyl]amino}-4,5-dihydronaphtho[1,2-d][1,3]thiazol-6-yl)acetamide,
N-(8-Nitro-4,5-dihydroaphtho[1,2-d][1,3]thiazol-2-yl)-4-propylbenzenesulfonamide,
N-(8-Nitro-4,5-dihyronaphtho[1,2-d][1,3]thiazol-2-yl)[1,1'-biphenyl]-4-sulfonamide.

Another object of the present invention is a compound as described above for medical use.

The compounds described above can be prepared by methods comprising at least one of the following steps:

a) sulfonamide coupling by reacting a 2-aminothiazole with a sulfonylchloride in the presence of a base, b) sulfonamide coupling by reacting a 2-aminothiazole derivative with a sulfonylchloride in the presence of a base, c) formation of a thiazole ring by reacting an optionally substituted thiourea with an α-haloketone, d) formation of a thiazole ring by reacting a thiourea with a ketone.

Another object of the present invention is a method for the treatment or prevention of diabetes, syndrome X, obesity, glaucoma, hyperlipidemia, hyperglycemia, hyperinsulinemia, osteoporosis, tuberculosis, depression, virus diseases and inflammtory disorders, said method comprising administering to a mammal, including man, in need of such treatment an effective amount of a compound of the formula (I)

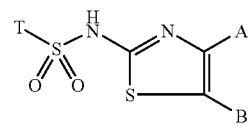

wherein

T is an aryl ring or heteroaryl ring, optionally independenty substituted by [R]$_n$, wherin n is an integer 0–5, and R is hydrogen, halogen, $C_{1-6}$-alkyl, and aryl;

A is selected from an aryl ring or heteroaryl ring, which can further be optionally substituted in one or more positions independently of each other by hydrogen, $C_{1-6}$-alkyl, halogenated $C_{1-6}$-alkyl, halogen, $C_{1-6}$-alkoxy, nitro, $C_{1-6}$-alkoxycarbonyl, $C_{1-6}$-alkylsulfonyl, acetylamino or aryloxy, wherein the aryloxy can further be optionally substituted in one or more positions independently of each other by hydrogen and halogen;

B is selected from hydrogen and $C_{1-6}$-alkoxycarbonyl or is linked to A to give a 6-membered aromatic or non-aromatic ring;

as well as pharmaceutically acceptable salts, hydrates and solvates thereof.

These compounds may also be used in the in the manufacture of a medicament for the treatment or prevention of diabetes, syndrome X, obesity, glaucoma, hyperlipidemia, hyperglycemia, hyperinsulinemia, osteoporosis, tuberculosis, depression, virus diseases and inflammatory disorders.

It is preferred that:

T is selected from thienyl substituted with one or more of bromo, chloro;
phenyl optionally substituted with one or more of chloro, methyl, propyl, phenyl, bromo, fluoro;
A is selected from 1-benzothien-3-yl, 3-(2,5-dimethylfuryl), pyridinyl;
thienyl optionally substituted with one or more of chloro, methylsulfonyl;
phenyl optionally substituted with one or more of ethoxycarbonyl, nitro, fluoro, methyl, methoxy, acetylamino, chloro, 4-chlorophenoxy, trifluoromethyl;
B is selected from hydrogen, carbethoxy or is linlked to A to give a 6-membered aromatic or non-aromatic ring.

Specific examples of compounds according to the present invention are:

Ethyl 2-(2-{[(4-chlorophenyl)sulfonyl]amino}-1,3-thiazol-4-yl)benzoate,
2,5-Dichloro-N-[4-(3-chloro-2-thienyl)-1,3-thiazol-2-yl]benzenesulfonamide,
4-Chloro-N-[4-(4,5-dichloro-2-thienyl)-1,3-thiazol-2-yl]benzenesulfonamide,
Ethyl 2-{[(4-chlorophenyl)sulfonyl]amino}-4-phenyl-1,3-thiazole-5-carboxylate,
Ethyl 2-{[(3-chloro-2-methylphenyl)sulfonyl]amino}-4-phenyl-1,3-thiazole-5-carboxylate,
N-[4-(3-nitrophenyl)-1,3-thiazol-2-yl]-4-propylbenzenesulfonamide,
N-(4-phenyl-1,3-thiazol-2-yl)-4-propylbenzenesulfonamide,
N-[4-(4-fluoro-3-methylphenyl)-1,3-thiazol-2-yl]-4-propylbenzenesulfonamide,
N-[4-(4--methoxyphenyl)-1,3-thiazol-2-yl]-4-propylbenzenesulfonamide,
3-Chloro-2-methyl-N-[4-(3-nitrophenyl)-1,3-thiazol-2-yl]benzesulfonamide,
3-Chloro-2-methyl-N-(4-phenyl-1,3-thiazol-2-yl)benzenesulfonamide,
3-Chloro-N-[4-(4-fluoro-3-methylphenyl)-1,3-thiazol-2-yl]-2-methylbenzenesulfonamide,
2,4,6-Trichloro-N-[4-(3-nitrophenyl)-1,3-thiazol-2-yl]benzenesulfonamide,
2,4,6-Trichloro-N-(4-phenyl-1,3-thiazol-2-yl)benzenesulfonamide,
2,4,6-Trichloro-N-[4-(4-fluoro-3-methylphenyl)-1,3-thiazol-2-yl]benzenesulfonamide,
2,4,6-Trichloro-N-[4-(4-methoxyphenyl)-1,3-thiazol-2-yl]benzenesulfonamide,
N-[4-(3-nitrophenyl)-1,3-thiazol-2-yl][1,1'-biphenyl]-4-sulfonamide,
N-(4-phenyl-1,3-thiazol-2-yl)[1,1'-biphenyl]-4-sulfonamide,
N-[4-(4-Fluoro-3-methylphenyl)-1,3-thiazol-2-yl][1,1'-bipheny]-4-sulfonamide,
N-[4-(4-Methoxyphenyl)-1,3-thiazol-2-yl][1,1'-biphenyl]-4-sulfonamide,
2,4-Dichloro-6-methyl-N-[4-(3-nitrophenyl)-1,3-thiazol-2-yl]benzenesulfonamide,
2,4-Dichloro-6-methyl-N-(4-phenyl-1,3-thiazol-2-yl)benzenesulfonamide,
2,4-Dichloro-N-[4-(4-fluoro-3-methylphenyl)-1,3-thiazol-2-yl]-6-methylbenzenesulfonamide,
2,4-Dichloro-N-[4-(4-methoxyphenyl)-1,3-thiazol-2-yl]-6-methylbenzenesulfonamide,
N-[4-(2-{[(4-propylphenyl)sulfonyl]amino}-1,3-thiazol-4-yl)phenyl]acetamide,
4-Propyl-N-[4-(3-pyridinyl)-1,3-thiazol-2-yl]benzenesulfonamide,
N-[4-(2-chloro-5-nitrophenyl)-1,3-thiazol-2-yl]-4-propylbenzenesulfonamide,
N-(7-methoxy-4,5-dihydronaphtho[1,2-d][1,3]thiazol-2-yl)-4-propylbenzenesulfonamide,
N-[4-(5-chloro-2-thienyl)-1,3-thiazol-2-yl]-4-propylbenzenesulfonamide,
N-[4-(2-chlorophenyl)-1,3-thiazol-2-yl]-4-propylbenzenesulfonamide,
N-[4-(2-{[(3-chloro-2-methylphenyl)sulfonyl]amino}-1,3-thiazol-4-yl)phenyl]acetamide,
3-Chloro-2-methyl-N-[4-(3-pyridinyl)-1,3-thiazol-2-yl]benzenesulfonamide,
3-Chloro-N-[4-(2-chloro-5-nitrophenyl)-1,3-thiazol-2-yl]-2-methylbenzenesulfonamide,
3-Chloro-N-(7-methoxy-4,5-dihydronaphtho[1,2-d][1,3]thiazol-2-yl)-2-methylbenzenesulfonamide,
3-Chloro-N-[4-(5-chloro-2-thienyl)-1,3-thiazol-2-yl]-2-methylbenzenesulfonamide,
3-Chloro-N-[4-chlorophenyl)-1,3-thiazol-2-yl]-2-methylbenzenesulfonamide,
N-[4-(2-{[(2,4,6-trichlorophenyl)sulfonyl]amino}-1,3-thiazol-4-yl)phenyl]acetamide,
2,4,6-Trichloro-N-[4-(3-pyridinyl)-1,3-thiazol-2-yl]benzenesulfonamide,
2,4,6-Trichloro-N-[4-(2-chloro-5-nitrophenyl)-1,3-thiazol-2-yl]benzenesulfonamide,
2,4,6-Trichloro-N-(7-methoxy-4,5-dihydronaphtho[1,2-d][1,3]thiazol-2-yl)benzenesulfonamide,
2,4,6-Trichloro-N-[4-(5-chloro-2-thienyl)-1,3-thiazol-2-yl]benzenesulfonamide,
2,4,6-Trichloro-N-[4-(2-chlorophenyl)-1,3-thiazol-2-yl]benzenesulfonamide,
N-(4-{2-[([1,1'-biphenyl]-4-ylsulfonyl)amino]-1,3-thiazol-4-yl}phenyl)acetamide,
N-[4-(3-pyridinyl)-1,3-thiazol-2-yl][1,1'-biphenyl]-4-sulfonamide,
N-[4-(2-chloro-5-nitrophenyl)-1,3-thiazol-2-yl][1,1'-biphenyl]-4-sulfonamide,
N-(7-methoxy-4,5-dihydronaphtho[1,2-d][1,3]thiazol-2-yl)[1,1'-biphenyl]-4-sulfonamide,
N-[4-(5-chloro-2-thienyl)-1,3-thiazol-2-yl][1,1'-biphenyl]-4-sulfonamide,
N-[4-(2-chlorophenyl)-1,3-thiazol-2-yl][1,1'-biphenyl]-4-sulfonamide,
N-[4-(2-{[(2,4-dichloro-6-methylphenyl)sulfonyl]amino}-1,3-thiazol-4-yl)phenyl]acetamide,
2,4-Dichloro-6-methyl-N-[4-(3-pyridinyl)-1,3-thiazol-2-yl]benzenesulfonamide, 2,4-Dichloro-N-[4-(2-chloro-5-nitrophenyl)-1,3-thiazol-2-yl]-6-methylbenzenesulfonamide,
2,4-Dichloro-N-(7-methoxy-4,5-diidronaphtho[1,2-d][1,3]thiazol-2-yl)-6-methylbenzenesulfonamide,
2,4-Dichloro-N-[4-(5-chloro-2-thienyl)-1,3-thiazol-2-yl]-6-methylbenzenesulfonamide,
2,4-Dichloro-N-[4-(2,5-dimethyl-3-furyl)-1,3-thiazol-2-yl]-6-methylbenzenesulfonamide,
N-[4-(1-benzothien-3-yl)-1,3-thiazol-2-yl]-2,4-dichloro-6-methylbenzenesulfonamide,
N-[4-(3-chloro-2-thienyl)-1,3-thiazol-2-yl]-4-propylbenzenesulfonamide,
3-Chloro-N-[4-(3-chloro-2-thienyl)-1,3-thiazol-2-yl]-2-methylbenzenesulfonamide,
2,4,6-Trichloro-N-[4-(3-chloro-2-thienyl)-1,3-thiazol-2-yl]benzenesulfonamide,
2,4-Dichloro-N-[4-(3-chloro-2-thienyl)-1,3-thiazol-2-yl]-6-methylbenzenesulfonamide,
2,4-Dichloro-N-[4-(2-chlorophenyl)-1,3-thiazol-2-yl]-6-methylbenzenesulfonamide,
Ethyl 2-[([1,1'-biphenyl]-4-ylsulfonyl)amino]-4-phenyl-1,3-thiazole-5-carboxylate,
3-Chloro-N-[4-(4-methoxyphenyl)-1,3-thiazol-2-yl]-2-methylbenzenesulfonamide,
N-[4-(2-{[(4-Bromo-2,5-difluorophenyl)sulfonyl]amino}-1,3-thiazol-4-yl)phenyl]acetamide,
2,3,4-Trichloro-N-[4-(2-chlorophenyl)-1,3-thiazol-2-yl]benzenesulfonamide,
2,4,5-Trichloro-N-[4-(3-chloro-2-thienyl)-1,3-thiazol-2-yl]benzenesulfonamide,
2,3,4-Trichloro-N-[4-(3-chloro-2-thienyl)-1,3-thiazol-2-yl]benzenesulfonamide,
4-Bromo-N-[4-(3-chloro-2-thienyl)-1,3-thiazol-2-yl]-2,5-difluorobenzenesulfonamide,
4,5-Dichloro-N-(7-methoxy-4,5-dihydronaphtho[1,2-d][1,3]thiazol-2-yl)-2-thiophenesulfonamide,
4,5-Dichloro-N-[4-(2-chlorophenyl)-1,3-thiazol-2-yl]-2-thiophenesulfonamide,
N-[2-{[(2,4,5-Trichlorophenyl)sulfonyl]amino}-1,3-thiazol-4-yl)phenyl]acetamide,
2,3,4-Trichloro-N-(7-methoxy-4,5-diydronaphtho[1,2-d][1,3]thiazol-2-yl)benzenesulfonamide,
4-Bromo-5-chloro-N-[4-(3-chloro-2-thienyl)-1,3-thiazol-2-yl]-2-thiophenesulfonamide,
3-Bromo-5-chloro-N-(7-methoxy-4,5-diydronaphto[1,2-d][1,3]thiazol-2-yl)-2-thiophenesulfonamide,
3-Bromo-5-chloro-N-[4-(2-chlorophenyl)-1,3-thiazol-2-yl]-2-thiophenesulfonamide,
N-[4-(2-{[(2,6-Dichlorophenyl)sufonyl]amino}-1,3-thiazol-4-yl)phenyl]acetamide,
2,6-Dichloro-N-[4-(3-chloro-2-thienyl)-1,3-thiazol-2-yl]benzenesulfonamide,
2,4,6-Trichloro-N-(7,8-dimethoxy-4,5-dihydronaphtho[1,2-d][1,3]thiazol-2-yl)benzenesulfonamide,
2,3,4-Trichloro-N-{4-[2-chloro-4-(4-chlorophenoxy)phenyl]-1,3-thiazol-2-yl)benzenesulfonamide,
2,3,4-Trichloro-N-{4-[2,6-dichloro-4-(trifluoromethyl)phenyl]-1,3-thiazol-2-yl}benzenesulfonamide,
N-[4-(2-Chloro-6-fluorophenyl)-1,3-thiazol-2-yl]-4-propylbenzenesulfonamide,
4-Bromo-N-{4-[2-chloro-4-(4-chlorophenoxy)phenyl]-1,3-thiazol-2-yl}-2,5-difluorobenzenesulfonamide,
4-Bromo-N-{4-[2,6-dichloro-4-(trifluoromethyl)phenyl]-1,3-thiazol-2-yl}-2,5-difluorobenzenesulfonamide,
4,5-Dichloro-N-[4-(2-chloro-6-fluorophenyl)-1,3-thiazol-2-yl]-2-thiophenesulfonamide,
4-Bromo-5-chloro-N-{4-[2-chloro-4-(4-chlorophenoxy)phenyl]-1,3-thiazol-2-yl)-2-thiophenesulfonamide,
4-Bromo-5-chloro-N-{4-[2,6-dichloro-4-(trifluoromethyl)phenyl]-1,3-thiazol-2-yl}-2-thiophenesulfonamide,
2,4-Dichloro-N-[4-(2-chloro-6-fluorophenyl)-1,3-thiazol-2-yl]-6-methylbenzenesulfonamide,
2,4,6-Trichloro-N-{4-[2,6-dichloro-4-(tifluoromethyl)phenyl]-1,3-thiazol-2-yl}benzenesulfonamide,
4-Bromo-N-[4-(2-chloro-6-fluorophenyl)-1,3-thiazol-2-yl]-2-methylbenzenesulfonamide,
2,4,6-Trichloro-N-{4-[2-chloro-4-(4-chlorophenoxy)phenyl]-1,3-thiazol-2-yl}benzenesulfonamide,
N-[4-(2-{[(4-Bromo-5-chloro-2-thienyl)sulfonyl]amino}-1,3-thiazol-4-yl)phenyl]acetamide,
N-(4,5-Dihydrothieno[3,2-e][1,3]benzothiazol-2-yl)benzenesulfonamide,
3,4-Dichloro-N-(4,5-diydrothieno[3,2-e][1,3]benzothiazol-2-yl)benzenesulfonamide,
3-Chloro-N-(4,5-dihydrothieno[3,2-e][1,3]benzothiazol-2-yl)-2-methylbenzenesulfonamide,
2,4,6-Trichloro-N-(4,5-diydrothieno[3,2-e][1,3]benzothiazol-2-yl)benzenesulfonamide,
N-(4,5-Dihydrothieno[3,2-e][1,3]benzothiazol-2-yl)[1,1'-biphenyl]-4-sulfonamide,
2,4-Dichloro-N-(4,5-dihydrothieno[3,2-e][1,3]benzothiazol-2-yl)-6-methylbenzenesulfonamide,
N-(4,5-Dihydrothieno[3,2-e][1,3]benzothiazol-2-yl)-4-propylbenzenesulfonamide,
3-Chloro-N-[6-chloro-8-(methylsulfonyl)-4,5-dihydrothieno[3,4-e][1,3]benzothiazol-2-yl]-2-methylbenzenesulfonamide,
N-[6-Chloro-8-(methylsulfonyl)-4,5-dihydrothieno[3,4-e][1,3]benzothiazol-2-yl]-4-propylbenzenesulfonamide,
2,4-Dichloro-N-[6-chloro-8-(methylsulfonyl)-4,5-diydrothieno[3,4-e][1,3]benzothiazol-2-yl]-6-methylbenzenesulfonamide,
N-[6-Chloro-8-methylsulfonyl-4,5-dihydrothieno[3,4-e][1,3]benzothiazol-2-yl][1,1'-biphenyl]-4-sulfonamide,
N-{2-[(Phenylsulfonyl)aminom]-4,5-dihydronaphtho[1,2-d][1,3]thiazol-6-yl}acetamide,
N-(2-{[(3-Chloro-2-methylphenyl)sulfonyl]amino}naphtho[1,2-d][1,3]thiazol-6-yl)acetamide,
N-(2-{[(4-Propylphenyl)sulfonyl]amino}-4,5-dihydronaphtho[1,2-d][1,3]thiazol-6-yl)acetamide,
N-(8-Nitro-4,5-dihydronaphtho[1,2-d][1,3]thiazol-2-yl)-4-propylbenzenesulfonamide,
N-(8-Nitro-4,5-dihydronaphtho[1,2-d][1,3]thiazol-2-yl)benzenesulfonamide,
N-(8-Nitro-4,5-dihydronaphtho[1,2-d][1,3]thiazol-2-yl)[1,1'-biphenyl]-4-sulfonamide.

Another object of the present invention is a pharmaceutical composition comprising at least one compound of the formula (I) as defined above, and a pharmaceutically acceptable carrier.

The compounds according to the present invention may be used in several indications which involve 11β-hydroxysteroid dehydrogenase type 1 enzyme. Thus the compounds accoding to the present invention may be used against dementia (see WO97/07789), osteoporosis (see Canalis E 1996, Mechanisms of glucocorticoid action in bone: implications to glucocorticoid-induced osteoporosis, Jounal of Clinical Endocrinology and Metabolism, 81, 3441–3447) and may also be used disorders in the immune system (see Franchimont et al, "Inhibition of Th1 immune response by glucocorticoids: dexamethasone selectively inhibits IL-12-induced Stat 4 phosphorylation in T lymphocytes", The journal of Immunology 2000, Feb 15, vol 164 (4), pages 1768–74) and also in the above listed indications.

The various terms used, separately and in combinations, in the above definition of the compounds having the formula (I) will be explained.

The term "aryl" in the present description is intended to include aromatic rings (monocyclic or bicyclic) having from 6 to 10 ring carbon atoms, such as phenyl (Ph) and naphthyl, which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetazole, chroman, isochroman, quinoline, quinoxaline, isoquinoline, phthalazine, cinnoline, quinazoline, indole, isoindole, indoline, isoindoline, benzothiophene, benzofuran, isobenzofuran, benzoxazole, 2,1,3-benzoxadiazole, benzothiazole, 2,1,3-benzothiazole, 2,1,3-benzoselenadiazole, benzimidazole, indazole, benzodioxane, indane, 1,2,3,4-tetrahydroquinoline, 3,4-dihydro-2 H-1,4-benzoxazine, 1,5-naphthyridine, 1,8-naphthyridine, acridine, fenazine and xanthene.

The term "heterocyclic" in the present description is intended to include unsaturated as well as partially and fully saturated mono-, bi- and tricyclic rings having from 4 to 14, preferably 4 to 10 ring atoms, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine and 1,4-oxazepane.

$C_{1-6}$-alkyl in the compound of formula (I) according to the present application, which may be straight, branched or cyclic, is preferably $C_{1-4}$-alkyl. Exemplary alkyl groups include methyl, ethyl, n-propyl, isopropyl, n-butyl, sec-butyl, tert-butyl, pentyl, isopentyl, hexyl, isohexyl, and cyclohexyl.

$C_{1-6}$-alkoxy, in the compound of formula (I) according to the present application may be straight or branched, is preferably $C_{1-4}$-alkoxy. Exemplary alkoxy groups include methoxy, ethoxy, propoxy, isopropoxy, butoxy, sec-butoxy, tert-butoxy, pentyloxy, isopentyloxy, hexyloxy, and isohexyloxy.

$C_{1-6}$-acyl, in the compound of formula (I) according to the present application may be saturated or unsaturated and is preferably $C_{1-4}$-acyl. Exemplary acyl groups include formyl, acetyl, propionyl, butyryl, isobutyryl, valeryl, isovaleryl, butenoyl (e.g. 3-butenoyl), hexenoyl (e.g. 5-hexenoyl).

The term "halogen" in the present description is intended to include fluorine, chlorine, bromine and iodine.

With the expression mono- or di-substituted is meant in the present description that the functionalities in question may be substituted wfth independently H, $C_{1-6}$-acyl, $C_{1-6}$-alkenyl, $C_{1-6}$-cyclo)alkyl, aryl, pyridylmethyl, or heterocyclic rings e.g. azetidine, pyrrolidine, piperidine, piperazine, morpholine and thiomorpholine, which heterocyclic rings optionally may be substituted with $C_{1-6}$-alkyl.

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, $8^{th}$ ed, McGraw-Hill Int. Ed 1992, "Biotransformation of Drugs, p. 13–15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like.

Pharmaceutical compositions according to the present invention contain a pharmaceutically acceptable carier together with at least one of the compounds comprising the formula (I) as described herein above, dissolved or dispersed therein as an active, antimicrobial, ingredient. In a preferred embodiment, the therapeutic composition is not immunogenic when administered to a human patient for therapeutic purposes, unless that purpose is to induce an immune response.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of auxiliary substances such as wetting or emulsifying agents, pH buffering agents and the like which enhance the effectiveness of the active ingredient. Adjuvants may also be present in the composition.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (I), may include pharmaceutically acceptable salts of that component therein as set out above. Phamaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes which are known for the skilled person in the art are thinkable.

The orally administerable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, sorbitol or glycine; tabletting lubricant e.g. magnesium stearate, talc, polyethylene glycol or silica; disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose, glucose syrup, gelatin hydrogenatd edible fats; emulsifying agents e.g. lecithin, sorbitan monooleate or acacia, non-aqueous vehicles (which may include edible oils), e.g. almond oil, fractionated coconut oil, oily esters such as glycerine, propylene glycol, or ethyl alcohol; preservatives e.g. methyl or propyl p-hydroxybenzoate or sorbic acid, and if desired conventional flavouring or colouring agents.

A pharmaceutical composition according to the present invention, may comprise typically an amount of at least 0.1 weight percent of compound comprising the formula (I) per weight of total therapeutic composition. A weight percent is a ratio by weight of total composition. Thus, for example, 0.1 weight percent is 0.1 grams of compound comprising the formula (I) per 100 grams of total composition. A suitable daily oral dose for a mammal, preferably a human being, may vary widely depending on the condition of the patient. However a dose of compound comprising the formula (I) of about 0.1 to 300 mg/kg body weight may be appropriate.

The compositions according to the present invention may also be used veterinarily and thus they may compnse a veterinarily acceptable excipient or carrier.

The compounds of the present invention in labelled form, e.g. isotopically labelled, may be used as a diagnostic agent.

The compounds of the formula (I) above may be prepared by, or in analogy with, conventional methods, and especially according to or in analogy with the following methods. Further, the pharmacology in-vitro was studied using the following reagents and methods.

All publications mentioned herein are hereby incorporated by reference. By the expression "comprising" we understand including but not limited to. Thus, other non-mentioned substances, additives or carriers may be present.

The invention will now be described in reference to the following Figures and Examples. These Figures and Examples are not to be regarded as limiting the scope of the present invention, but shall only serve in an illustrative manner.

EXPERIMENTAL METHODS

Scintillation Proximity Assay

[1, 2(n) -$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β- $HSD_1$) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a Wallac-Qunadra. The amount of the product [$^3$H]cortisol, bound to the beads was determined in a Packard, Top Count microplate liquid scintillation counter.

The 11-β-$HSD_1$ enzyme assay was carried out in 96 well microtiter plates Packard, Optiplate) in a total well volume of 220 μL and contained 30 mM Tris-HCl, pH 7.2 with 1 mM EDTA, a substrate mixture tritiated Cortisone/NADPH (175 nM/181 μM), G-6-P (1 mM) and inhibitors in serial dilutions (9 to 0.15 μM). Reactions were initiated by the addition of human 11-β-$HSD_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 μL 1 mM GA stop solution. Monoclonal mouse antibody was then added (10 μL of 4 μM followed by 100 μL of SPA beads (suspended according to the manufacturers instructions). Appropriate controls were set up by omitting the 11-β-$HSD_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter.

The calculation of the $K_i$ values for the inhibitors was performed by use of Activity Base. The $K_i$ value is calculated fom $IC_{50}$ and the $K_m$ value is calculated using the Cheng Prushoff equation (with reversible inhibition that follows the Michaelis-Menten equation):

$$K_i = IC_{50}(1+[S]/K_m)$$

[Cheng, Y. C.; Prushoff, W. H. Biochem. Phamacol. 1973, 22, 3099–3108]. The $IC_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 μM. Illustrative of the invention, the following Ki values have been determined in the human 11-β-HSD1 enzyme assay (see Table 1):

Table 1: Ki values determined in the human 11-β-HSD1 enzyme assay.

| Compound of Example | K$_i$ (uM) |
|---|---|
| 14 | 163 |
| 28 | 14 |
| 30 | 91 |

COMPOUND PREPARATION

General

For preparative straight phase HPLC purification a Phenomenex column (250×21.1 mm, 10 μm) was used on a Gilson system eluting with ethanol in chloroform (gradient from 0–10 min 10 min) with a flow of 20 mL/min. Column chromatography was performed on silica using Silica gel 60 (230–400 mesh), Merck. Melting points were determined on a Gallenkamp apparatus. Elemental analyses were recorded using a Vario EL instrument HPLC analyses were performed using a Hypersil Elite column (150×4.6 mm, 3 μ) with a flow of 3 mL/min on a Waters 600E system with monitoring at 254 nm. Reverse phase preparative HPLC was carried out on a 100×21.2 mm, 5 μ Hypersil Elite column eluting with a gradient of 5% ACN in 95% water to 95% ACN in 5% water (0.2% TFA buffer) over 10 mins at a flow rate of 20 mL/min with the UV detector set at 254 nm. Thin layer chromatography was carried out using pre-coated silica gel F-254 plates (thickness 0.25 mm). Electrospray MS spectra were obtained on a Micromass platform LCMS spectrometer, Crude, worked up compounds were purified by flash column chromatography usng pre packed silica SPE columns (10 g silica) on an Isco Foxy 200 Combiflash system, and a gradient of 16.67% ethyl acetate in hexane increasing incrementally to 100% ethyl acetate.

List Of Abbreviations

DCM=dichloromethane
DMAP=4-dimethylaminopyridine
DMF=dimethylformamide
DMSO=dimethyl sulfoxide EDTA=ethylenediaminetetraacetic acid

SULFONAMIDE COUPLINGS

Method A

1 Eq of the 2-aminothiazole was dissolved in pyridine (0.5 M solution). The sulfonyl chloride (1.2 eq) was added and the reaction mixture was stirred at ambient temperature under nitrogen atmosphere for 15 h. The reaction mixture was poured into aqueous HCl (1 M). If the product precipitated it was collected on a filter and washed with aqueous HCl (1 M) and recrystallised from ethanol. In case an oil was obtained, the crude was extracted with DCM and worked up and purfied using standard procedures.

Method B

A solution of the 2-aminothiazole derivative (1 eq), triethylamine (2 eq) and DMAP (1 eq) in DMF (1 M) and DCM (0.225 M) was dispensed into a reaction vial. The sulfonyl chloride (1.2 eq) was dissolved in DCM (0.33 M) and added. The reaction mixtures were kept at room temperature over night. The mixture was then added to petroleum ether (10 times reaction volume). After some hours in refrigerator the supernatants were decanted and (a portion of) the residual materials were dissolved in DMSO-methanol-acetic acid (300 μL+500 μL+50 μL) and purified by preparative LCMS (acetonitrile-water gradients). The purest fractions were collected and lyophilized. Alternatively, the crude was isolated using extractive work up and purified using standard procedures.

FORMATION OF THIAZOLE RING

Method H

To a solution or suspension of a (substituted) thiourea in ethanol (0.5 M), 1 equivalent of α-haloketone was added at room temperature. The reaction mixture was stirred in a sealed tube at 95° C. for 4 h, cooled, concentrated, redissolved in ethyl acetate, washed with saturated aqueous sodium hydrogen carbonate, dried over sodium sulfate and chromatographed on silica gel using petroeum-ether and ethyl acetate as eluents.

Method I

To a 0.5 M solution of ketone (1 eq) and thiourea (2 eq) in ethanol at 60° C., 1 eq of iodine was added in one portion. The reaction tube was sealed and the reaction mixture was stirred at 100° C. for 16 hours. After evaporation of the solvent the residue was taken up in DCM, washed with saturated aqueous sodium hydrogen carbonate, dried with magnesium sulfate. Products were purified by chromatography on silica gel using a gradient of petroleum-ether/ethyl acetate from 8:1 to 2:1 for elution.

KNOWN EXAMPLES

The conpounds of the followmg Examples 1–3 [244A–246A] are commercially available and could e g be purchased from Bionet (Example 1 and 2) or Maybridge (Example 3).

1 [244A] Ethyl 2-(2-{[(4-chlorophenyl)sulfonyl]amino}-1,3-thiazol-4-yl)benzoate
2 [245A] 2,5-Dichloro-N-[4-(3-chloro-2-thienyl)-1,3-thiazol-2-yl]benzenesulfonamide
3 [246A] 4-Chloro-N-[4-(4,5-dichloro-2-thienyl)-1,3-thiazol-2-yl]benzenesulfonamide

NOVEL EXAMPLES

The following specific compounds were synthesized The commercially available compounds thus only form embodiments, as indicated earlier in the description, as pharmaceutical preparations and use of said compounds as set out in the appended set of claims.

EXAMPLE 4 [248A]

Ethyl 2-{[(4-chlorophenyl)sulfonyl]amino}-4-phenyl-1,3-thiazole-5-carboxylate

The title compound was prepared from ethyl 2-amino-4-phenylthiazole-5-carboxylate and 4-chlorobenzenesulfonyl chloride as described in the synthetic METHOD B to give a white solid (61.7 mg) with purity >90%. LCMS (pos) m/z 423.0.

EXAMPLE 5 [250A]

Ethyl 2-{[(3-chloro-2-methylphenyl)sulfonyl]amino}-4-phenyl-1,3-thiazole-5-carboxylate The title compound was prepared from ethyl 2-amino-4-phenylthiazole-5-carboxylate and 3-chloro-2-methylbenzenesulfonyl chloride as described in the synthetic METHOD B to give a white solid (47.2 mg) with purity >90%. LCMS (pos) m/z 437.0.

EXAMPLE 6 [252A]

N-[4-(3-nitrophenyl)-1,3-thiazol-2-yl]-4-propylbenzenesulfonamide

The title compound was prepared from 2-amino-4-(3-nitrophenyl)thiazole and 4-n-propylbenzenesulfonyl chloride as described in the synthetic METHOD B to give a yellow solid (41.5 mg) with purity >90%: MS (pos) m/z 404.1, (neg) m/z 402.2; HRMS m/z 403.0062 (calc. of monoisotopic mass for $Cl_{18}H_{17}N_3O_4S_2$ gives 403.0060).

EXAMPLE 7 [253A]

N-(4-phenyl-1,3-thiazol-2-yl)-4-propylbenzenesulfonamide

The title compound was prepared from 2-amino-4-phenylthiazole and 4-n-propylbenzenesulfonyl chloride as described in the synthetic METHOD B to give a white solid (29.8 mg) with purity >90%. MS (pos) m/z 359.2.

EXAMPLE 8 [254A]

N-[4-(4-fluoro-3-methylphenyl)-1,3-thiazol-2-yl]-4-propylbenzenesulfonamide

The title compound was prepared from 2-amino-4-(4'-fluoro-3'-methyl)phenylthiazole and 4-n-propylbenzenesulfonyl chloride as described in the synthetic METHOD B to give a white solid (31.5 m) with puriy >90%. MS (pos) m/z 391.2.

EXAMPLE 9 [255A]

N-[4-(4-methoxyphenyl)-1,3-thiazol-2-yl]-4-propylbenzenesulfonamide

The title compound was prepared from 4(4-methoxyphenyl)-thiazol-2-ylamine and 4-n-propylbenzenesulfonyl chloride as described in the synthetic METHOD B to give a white solid (32.2 mg) with purity >90%. MS (pos) m/z 389.2.

EXAMPLE 10 [256A]

3-Chloro-2-methyl-N-[4-(3-nitrophenyl)-1,3-thiazol-2-yl]benzenesulfonamide

The title compound was prepared from 2-amino-4-(-3-nitrophenyl)thiazole and 3-chloro-2-methylbenzenesulfonyl chloride as described in the synthetic METHOD B to give a yellow solid (36.0 mg) with purity >90%. MS (pos) m/z 410.0.

EXAMPLE 11 [257A]

3-Chloro-2-methyl-N-(4-phenyl-1,3-thiazol-2-yl)benzenesulfonamide

The title compound was prepared from 2-amino-4-phenylthiazole and 3-chloro-2-methylbenzenesulfonyl chloride as described in the synthetic METHOD B to give a white solid (51.8 mg) with purity >90%. MS (pos) m/z 365.1.

EXAMPLE 12 [258A]

3-Chloro-N-[4-(4-fluoro-3-methylphenyl)-1,3-thiazol-2-yl]-2-methylbenzenesulfonamide The title compound was prepared from 2-amino-4-(4'-fluoro-3'-methyl)phenylthiazole and 3-chloro-2-methylbenzenesulfonyl chloride as described in the synthetic METHOD B to give a white solid (39.7 mg) with purity >90%. MS (pos) m/z 397.1.

EXAMPLE 13 [259A]

2,4,6-Trichloro-N-[4-(3-nitrophenyl)-1,3-thiazol-2-yl]benzenesulfonamide

The title compound was prepared from 2-amino-4-(3-nitrophenyl)thiazoe and 2,4,6-trichlorobenzenesulfonyl chloride as described in the synthetic METHOD B to give a yellow solid (16.2 mg) with purity >90%. MS (pos) m/z 465.9.

EXAMPLE 14 [260A]

2,4,6-Tricholro-N-(4-phenyl-1,3-thiazol-2-yl)benzenesulfonamide

The title compound was prepared from 2-amino-4-phenylthiazole and 2,4,6-trichlorobenzenesulfonyl chloride as described in the synthetic METHOD B to give a white solid (16.0 mg) with purity >90%. MS (pos) m/z 419.0, 421.0, 423.0.

EXAMPLE 15 261A]

2,4,6-Trichloro-N-[4-(4-fluoro-3-methylphenyl)-1,3-thiazol-2-yl]benzenesulfonamide The title compound was prepared from 2-amino-4-(4'-fluoro-3'-methyl)phenylthiazole and 2,4,6-trichlorobenzenesulfonyl chloride as described in the synthetic METHOD B to give a white solid (50.9 mg) with purity >90%: MS (pos) m/z 451.0, 453.0, 455.0; HRMS m/z 449.9218 (calc. of monoisotopic mass for $C_{16}H_{10}Cl_3FN_2O_2S_2$ gives 449.9233).

EXAMPLE 16 [262A]

2,4,6-Trichloro-N-[4-(4-methoxyphenyl)-1,3-thiazol-2-yl]benzenesulfonamide

The title compound was prepared from 4-(4-methoxyphenyl)-thiazol-2-ylamine and 2,4,6-trichlorobenzenesulfonyl chloride as described in the synthetic MEIHOD B to give a white-yellow solid (58.2 mg) with purity >90%. MS (pos) m/z 449.1, 451.1, 453.1.

EXAMPLE 17 [263A]

N-[4-(3-nitrophenyl)-1,3-thiazol-2-yl][1,1'-biphenyl]-sulfonamide

The title compound was prepared from 2-amino-4-(-3-nitrophenyl)thiazole and 4-phenylbenzenesulfonyl chloride as described in the synthetic METHOD B to give a yellow solid (25.8 mg) with purity >80%. MS (pos) m/z 438.1.

EXAMPLE 18 [264A]

N-(4-phenyl-1,3-thiazol-2-yl)[1,1'-biphenyl]-4-sulfonamide

The title compound was prepared from 2-aminoph-4-phenylthiazole and 4-phenylbenzenesulfonyl chloride as described in the synthetic METHOD B to give a white solid (32.9 mg) with purity >90%: MS (pos) m/z 393.2; HRMS m/z 392.0658 (calc. of monoisotopic mass for $C_{21}H_{16}N_2O_2S_2$ gives 392.0653).

EXAMPLE 19 [265A]

N-[4-(4-Fluoro-3-methylphenyl)-1,3-thiazol-2-yl][1,1'-biphenyl]-4-sulfonamide

The title compound was prepared from 2-amino-4-(4'-fluoro-3'-methyl)phenylthiazole and 4-phenylbenzenesulfonyl chloride as described in the synthetic METHOD B to give a white solid (15.8 mg) with purity >90%. MS (pos) m/z 425.2.

EXAMPLE 20 [266A]

N-[4-(4-Methoxyphenyl)-1,3-thiazol-2-yl][1,1'-biphenyl]-sulfonamide

The title compound was prepared from 4-(4-methoxyphenyl)-thiazol-2-ylamine 4-phenylbenzenesulfonyl chloride as described in the synthetic METHOD B to give a white solid (17.8 mg) with purity >90%. MS (pos) m/z 423.3.

EXAMPLE 21 [267A]

2,4-Dichloro-6-methyl-N-[4-(3-nitrophenyl)-1,3-thiazol-2-yl]benzenesulfonamide

The title compound was prepared from 2-amino-4-(-3-nitrophenyl)thiazole and 2,4-dichloro-6-methylbenzenesulfonyl chloride as described in the synthetic METHOD B to give a yellow solid (27.3 mg) with purity >90%. MS (pos) m/z 444.0, 446.0.

EXAMPLE 22 [268A]

2,4-Dichloro-6-methyl-N-(4-phenyl-1,3-thiazol-2-yl)benzenesulfonamide

The title compound was prepared from 2-amino-4-phenylthiazole and 2,4-dichloro-6-methylbenzenesulfonyl chloride as described in the synthetic METHOD B to give a white solid (49.2 mg) with purity >90%. MS (pos) m/z 399.1, 401.1.

EXAMPLE 23 [269A]

2,4-Dichloro-N-[4-(4-fluoro-3-methylphenyl)-1,3-thiazol-2-yl]-6-methylbenzenesulfonamide The title compound was prepared from 2-amino-4-(4'-fluoro-3'-methyl)phenylthiazole and 2,4-dichloro-6-methylbenzenesulfonyl chloride as described in the synthetic METHOD B to give a white solid (28.4 mg) with purity >90%. MS (pos) m/z 431.1, 433.1.

EXAMPLE 24 [270A]

2,4-Dichloro-N-[4-(4-methoxyphenyl)-1,3-thiazol-2-yl]-6-methylbenzenesulfonamide The title compound was prepared from 4-(4-methoxyphenyl)-thiazol-2-ylamine 2,4-dichloro-6-methylbenzenesulfonyl chloride as descnbed in the synthetic METHOD B to give a white solid (48.4 mg) with purity >90%: MS (pos) m/z 429.1, 431.1; HRMS m/z 427.9810 (calc. of monoisotopic mass for $C_{17}H_{14}Cl_2N_2O_3S_2$ gives 427.9823).

EXAMPLE 25 [271A]

N-[4-(2-{[(4-propylphenyl)sulfonyl]amino}-1,3-thiazol-4-yl)phenyl]acetamide

The title compound was prepared from N-[4-(2-amino-1,3-thiazol-4-yl)phenyl]acetamide and 4-n-propylbenzenesulfonyl chloride as described in the synthetic METHOD B to give a yellow solid (1.0 mg) with purity >80%. MS (pos) m/z 416.2.

EXAMPLE 26 [272A]

4-Propyl-N-[4-(3-pyridinyl)-1,3-thiazol-2-yl]benzenesulfonamide

The title compound was prepared from 4-(3-pyridyl)-1,3-thiazol-2-amine and 4-n-propylbenzenesulfonyl chloride as described in the synthetic METHOD B to give a white-yellow solid (2.3 mg) with purity >90%. MS (pos) m/z 360.2.

EXAMPLE 27 273A]

N-[4-chloro-5-nitrophenyl)-1,3-thiazol-2-yl]-4-propylbenzenesulfonamide

The title compound was prepared from 4-(2-chloro-5-nitrophenyl)-1,3-thiazol-2-amine hydrobromide and 4-n-propylbenzenesulfonyl chloride as described in the synthetic METHOD B to give a white solid (9.0 mg) with purity >90%. MS (pos) m/z 438.2.

EXAMPLE 28 274A]

N-(7-methoxy-4,5-dihydronsphthol[1,2-d][1,3]thiazol-2-yl)4-propylbenzenesulfonamide The title compound was prepared from 7-methoxy-4,5-dihydronaphto{1,2-D][1,3]thiazol-2-amine hydrobromide and 4-n-propylbenzenesulfonyl chloride as described in the synthetic METHOD B to give a yellow solid (29.0 mg) with purity >90%: MS (pos) m/z 415.3; HRMS m/z 414.1068 (calc. of monoisotopic mass for $C_{21}H_{22}N_2O_3S_2$ gives 414.1072).

EXAMPLE 29 [275A]

N-[4-(5-chloro-2-thienyl)-1,3-thiazol-2-yl]-4-propylbenzenesulfonamide

The title compound was prepared from 4-(5-chloro-2-thienyl)-1,3-thiazol-2-amine and 4-n-propylbenzenesulfonyl chloride as described in the synthetic METHOD B to give a brown solid (16.4 mg) with purity >80%. MS (pos) m/z 399.2.

EXAMPLE 30 [276A]

N-[4-(2-chlorophenyl)-1,3-thiazol-2-yl]-4-propylbenzenesulfonamide

The title compound was prepared from 4-(2-chlorophenyl)-1,3-thiazol-2-amine and 4-n-propylbenzenesulfonyl chloride as described in the synthetic METHOD B to give a white solid (30.9 mg) with purity >90%. MS (pos) m/z 393.1.

EXAMPLE 31 [277A]

N-[4-(2-{[(3-chloro-2-methylphenyl)sulfonyl]amino}-1,3-thiazol-4-yl)phenyl]acetamide The title compound was prepared N-[4-(2-amino-1,3-thiazol-4-yl)penyl]acetamide and 3-chloro-2-methylbenzenesulfonyl chloride as described in the synthetic METHOD B to give a white solid (16.1 mg) with purity >90%: MS (pos) m/z 422.1, (neg) m/z 420.3. HRMS m/z 421.0327 (calc. of monoisotopic mass for $C_{18}H_{16}ClN_3O_3S_2$ gives 421.0322).

EXAMPLE 32 [278A]

3-Chloro-2-methyl-N-[4-(3-pyridinyl)-1,3-thiazol-2-yl]benzenesulfonamide

The title compound was prepared from 4-(3-pyridyl)-1,3-thiazol-2-amine and 3-chloro-2-methylbenzenesulfonyl chloride as described in the synthetic METHOD B to give a yellow solid (21.4 mg) with purity >90%. MS (pos) m/z 366.1.

EXAMPLE 33 [279A]

3-Chloro-N-[4-(2-chloro-5-nitrophenyl)-1,3-thiazol-2-yl]-2-methylbenzenesulfonamide The title compound was prepared from 4-(2-chloro-5-nitrophenyl)-1,3-thiazol-2-amine hydrobromide and 3-chloro-2-methylbenzenesulfonyl chloride as described in the synthetic METHOD B to give a yellow solid (16.5 mg) with purity >90%. $^1$H-NMR (DMSO-$d_6$) δ 13.43 (s, NH), 8.46 (d, J=2.8 Hz, 1 H), 8.29 (d, J=2.8 Hz, 1 H), 7.96 (dd, J=1.1 Hz, J=8.0 Hz, 1 H), 7.90 (d, J=8.8 Hz, 1 H), 7.70 (dd, J=1.1 hz, J=8.0 Hz, 1 H), 7.42 (t, J=8.0 Hz, 1 H), 7.52 (s, 1 H), 2.67 (s, 3 H); MS (pos) m/z 442.2,444.2.

EXAMPLE 34 [280]

3-Chloro-N-(7-methoxy4,5-dihydronaphtho[1,2 -d][1,3]thiazol-2-yl)-2-methylbenzenesulfonamide The title compound was prepared from 7-methoxy-4,5-dihydronapho[1,2-D][1,3]thiazol-2-amine hydrobromide and 3-chloro-2-methylbenzenesulfonyl chloride as described in the synthetic METHOD B to give a white solid (30.7 mg) with purity >90%. MS (pos) m/z 421.1.

EXAMPLE 35 [281A]

3-Chloro-N-[4-(5-chloro-2-thienyl)-1,3-thiazol-2-yl]-2-methylbenzenesulfonamide

The title compound was prepared from 4-(5-chloro-2-thienyl)-1,3-thiazol-2-amine and 3-chloro-2-methylbenzenesulfonyl chloride as described in the synthetic METHOD B to give a beige solid (29.9 mg) with purity >90%: MS (pos) m/z 405.0, 407.0; HRMS m/z 403.9278 (calc. of monoisotopic mass for $C_{14}H_{10}Cl_2N_2O_2S_3$ gives 403.9281).

EXAMPLE 36 [282A]

3-Chloro-N-[4-(2-chlorophenyl)-1,3-thiazol-2-yl]-2-methylbenzenesulfonamide

The title compound was prepared from 4-(2-chlorophenyl)-1,3-thiazol-2-amine and 3-chloro-2-methylbenzenesulfonyl chloride as described in the synthetic METHOD B to give a white solid (45.3 mg) with purity >90%: MS (pos) m/z 399.1, 401.1; HRMS m/z 397.9711 (calc. of monoisotopic mass for $C_{16}H_{12}Cl_2N_2O_2S_2$ gives 397.9117).

EXAMPLE 37 [283A]

N-[4-{[(2,4,6-trichlorophenyl)sulfonyl]amino)-1,3-thiazol-4-yl)phenyl]acetamide

The title compound was prepared N-[4-(2-amino-1,3-thiazol-4-yl)phenyl]acetamide and 2,4,6-trichlorobenzenesulfonyl chloride as described in the synthetic METHOD B to give a yellow solid (2.5 mg) with purity >80%. MS (pos) m/z 476.1, 478.1, 480. 1.

EXAMPLE 38 [284A]

2,4,6-Trichloro-N-[4-(3-pyridinyl)-1,3-thiazol-2-yl]benzenesulfonamide

The title compound was prepared from 4-(3-pyridyl)-1,3-thiazol-2-amine and 2,4,6-trichlorobenzenesulfonyl chloride as described in the synthetic METHOD B to give a yellow solid (29.3 mg) with purity >90%: MS (pos) m/z 422.1; HRMS m/z 418.9134 (calc. of monoisotopic mass for $C_{14}H_8Cl_3N_3O_2S_2$ gives 418.9123).

EXAMPLE 39 [285A]

2,4,6-Trichloro-N-[4-(2-chloro-5-nitrophenyl)-1,3-thiazol-2-yl]benzenesulfonamide The title compound was prepared from 4-(2-chloro-5-nitrophenyl)-1,3-thiazol-2-amine hydrobromide and 2,4,6-trichlorobenzesulfonyl chloride as described in the synthetic METHOD B to give a yellow solid (11.3 mg) with purity >90%. MS (pos) m/z 498.0, 500.0, 502.0.

EXAMPLE 40 [286A]

2,4,6-Trichloro-N-(7-methoxy-4,5-dihydronaphtho[1,2-d][1,3]thiazol-2-yl)benzenesulfonamide The title compound was prepared from 7-methoxy4,5-dihydronaphto[1,2-D][1,3 1]thiazol-2-amine hydrobromide and 2,4,6-trichlorobenzenesulfonyl chloride as described in the synthetic METHOD B to give a yellow solid (10.1 mg) with purity >90%. MS (pos) m/z 477.1.

EXAMPLE 41 [287A]

2,4,6-Trichloro-N-[4-(5-chloro-2-thienyl)-1,3-thiazol-2-yl]benzenesulfonamide

The title compound was prepared from 4-(5-chloro-2-thienyl)-1,3-thiazol-2-amine and 2,4,6-trichlorobenzenesulfonyl chloride as described in the synthetic METHOD B to give a yellow solid (24.0 mg) with purity >90%. MS (pos) m/z 461.0, 463.0.

EXAMPLE 42 [289A]

2,4,6-Trichloro-N-[4-(2-chlorophenyl)-1,3-thiazol-2-yl]benzenesulfonamide

The title compound was prepared from 4-(2-chlorophenyl)-1,3-thiazol-2-amine and 2,4,6-trichlorobenzenesulfonyl chloride as described in the synthetic METHOD B to give a white solid (38.7 mg) with purity >90%. MS (pos) m/z 453.0, 455.0, 457.0.

EXAMPLE 43 [290A]

N-(4-{2-[([1,1'-biphenyl]-4-ylsulfonyl)amino]-1,3-thiazol-4-yl}phenyl)acetamide

The title compound was prepared N-[4-(2-amino-1,3-thiazol-4-yl)phenyl]acetamide and 4-phenylbenzenesulfonyl chloride as described in the synthetic METHOD B to give a white-yellow solid (8.6 mg) with purity >80%. MS (pos) m/z 450.3.

EXAMPLE 44 [291A]

N-[4-(3-pyridinyl)-l1,3-thiazol-2-yl][1,1'-biphenyl]sulfonamide

The title compound was prepared from 4-(3-pyridyl)-1,3-thiazol-2-amine and 4-phenylbenzenesulfonyl chloride as described in the synthetic METHOD B to give a white-yellow solid (1.4 mg) with purity >80%. MS (pos) m/z 394.2.

EXAMPLE 45 [292A]

N-[4-(2-chloro-5-nitrophenyl)-1,3-thiazol-2-yl][1,1'-biphenyl]-4-sulfonamide

The title compound was prepared from 4-(2-chloro-5-nitrophenyl)-1,3-thiazol-2-amine hydrobromide and 4-phenylbenzenesulfonyl chloride as described in the synthetic METHOD B to give a white solid (11.9 mg) with purity >90%. MS (pos) m/z 472.1.

EXAMPLE 46 [293A]

N-(7-methoxy-4,5-dihydronaphtho[1,2-d][1,3]thiazol-2-yl)[1,1'-biphenyl]-4-sulfonamide The title compound was prepared from 7-methoxy4,5-dihydronaphto[1,2-D][1,3]thiazol-2-amine hydrobromide and 4-phenylbenzenesulfonyl chloride as described in the synthetic METHOD B to give a white-yellow solid (17.0 mg) with purity >80%. MS (pos) m/z 449.2.

EXAMPLE 47 [294A]

N-[4-(5-chloro-2-thienyl)-1,3-thiazol-2-yl][1,1'-biphenyl]-4-sulfonamide

The title compound was prepared from 4-(5-chloro-2-thieny)-1,3-thiazol-2-amine and 4-phenylbenzenesulfonyl chloride as described in the synthetic METHOD B to give a white solid (4.3 mg) with purity >80%. MS (pos) m/z 433.1, 435.1.

EXAMPLE 48 [295A]

N-[4-2-chlorophenyl)-1,3-thiazol-2-yl][1,1'-biphenyl]-4-sulfonamide

The title compound was prepared from 4-(2-chlorophenyl)-1,3-thiazol-2-amine and 4-phenylbenzenesulfonyl chloride as described in the synthetic METHOD B to give a white solid (31.8 mg) with purity >90%. MS (pos) m/z 427.1.

EXAMPLE 49 [296A]

N-[4-(2-{[(2,4-dichloro-6-methylphenyl)sulfonyl]amino}-1,3-thiazol-4-yl)phenyl]acetamide The title compound was prepared N-[4-(2-amino-1,3-thiazol-4-yl)phenyl]acetamide and 2,4-dichloro-6-methylbenzenesulfonyl chloride as described in the synthetic METHOD B to give a white-yellow solid (8.1 mg) with purity >80%. MS (pos) m/z 456.2, 458.1.

EXAMPLE 50 [297A]

2,4-Dichloro-6-methyl-N-[4-(3-pyridinyl)-1,3-thiazol-2-yl]benzenesulfonamide

The title compound was prepared from 4-(3-pyridyl)-1,3-thiazol-2-amine and 2,4-dichloro-6-methylbenzenesulfonyl chloride as described in the synthetic METHOD B to give a yellow solid (17.6 mg) with purity >90%. MS (pos) m/z 400.0, 402.0.

EXAMPLE 51 [298A]

2,4-Dichloro-N-[4-(2-chloro-5-nitrophenyl)-1,3-thiazol-2-yl]-6-methylbenzenesulfonamide The title compound was prepared from 4-(2-chloro-5-nitrophenyl)-1,3-thiazol-2-amine hydrobromide and 2,4-dichloro-6-methylbenzenesulfonyl chloride as described in the synthetic METHOD B to give a white-yellow solid (18.4 mg) with purity >90%. MS (pos) m/z 478.0, 479.9.

EXAMPLE 52 [299A]

2,4-Dichloro-N-(7-methoxy-4,5-dihydronaphtho[1,2-d][1,3]thiazol-2-yl)-6-methylbenzenesulfonamide The title compound was prepared firom 7-methoxy-4,5-dihydronaphto[1,2-D][1,3]thiazol-2-amine hydrobromide and 2,4-dichloro-6-methylbenzenesulfonyl chloride as described in the synthetic METHOD B to give a white solid (16.3 mg) with purity >90%. MS (pos) m/z 455.1, 457.1.

EXAMPLE 53 [300A]

2,4-Dichloro-N-[4-(5-chloro-2-thienyl)-1,3-thiazol-2-yl]-6-methylbenzenesulfonamide The title compound was prepared from 4-(5-chloro-2-thienyl)-1,3-thiazol-2-amine (METHOD H) and 2,4-dichloro-6-methylbenzenesulfonyl chloride as described in the synthetic METHOD B to give a white solid (19.5 mg) with purity >90%. MS (pos) m/z 439.0, 441.0.

EXAMPLE 54 [301A]

2,4-Dichloro-N-[4-(2,5-dimethyl-3-furyl)-1,3-thiazol-2-yl]-6-methylbenzenesulfonamide The title compound was prepared from 4-(2,5-dimethyl-3-furyl)-1,3-thiazol-2-ylamine (METHOD I) and 2,4-dichloro-6-methylbenzenesulfonyl chloride as described in the synthetic METHOD B to give a yellow solid (11.6 mg) with purity >90%. MS (pos) m/z 417.1, 419.1.

EXAMPLE 55 [304A]

N-[4-(1-benzothien-3-yl)-1,3-thiazol-2-yl]-2,4-dichloro-6-methylbenzenesulfonamide The title compound was prepared from 4-(1-benzothien-3-yl)-1,3-thiazol-2-amine (METHOD I) and 2,4-dichloro-6-methylbenzenesulfonyl chloride as described in the synthetic METHOD B to give a white solid (47.0 mg) with purity >90%. MS (pos) m/z 455.0, 457.0.

EXAMPLE 56 [305A]

N-[4-(3-chloro-2-thienyl)-1,3-thiazol-2-yl]-4-propylbenzenesulfonamide

The title compound was prepared from 4-(3-chloro-2-thienyl)-1,3-thiazol-2-amine and 4-n-propylbenzenesulfonyl chloride as described in the synthetic METHOD B to give a brown-red solid (5.3 mg) with purity >90%. MS (pos) m/z 399.2, 401.2.

EXAMPLE 57 [306A]

3-Chloro-N-[4-(3-chloro-2-thienyl)-1,3-thiazol-2-yl]-2-methylbenzenesulfonamide

The title compound was prepared from 4-(3-chloro-2-thienyl)-1,3-thiazol-2-amine and 3-chloro-2-methylbenzenesulfonyl chloride as described in the synthetic METHOD B to give a white-yellow solid (7.6 mg) with purity >90%. MS (pos) m/z 405.2, 407.2.

EXAMPLE 58 [307A]

2,4,6-Trichloro-N-[4-(3-chloro-2-thienyl)-1,3-thiazol-2-yl]benzenesulfonamide

The title compound was prepared from 4-(3-chloro-2-thienyl)-1,3-thiazol-2-amine and 2,4,6-trichlorobenzenesulfonyl chloride as described in the synthetic METHOD B to give a white solid (5.0 mg) with purity >90%. MS (pos) m/z 459.1, 461.1, 463.1.

EXAMPLE 59 [308A]

2,4-Dichloro-N-[4-(3-chloro-2-thienyl)1,3-thiazol-2-yl]-6-methylbenzenesulfonamide The title compound was prepared from 4-(3-chloro-2-thienyl)-1,3-thiazol-2-amine and 2,4-dichloro-6-methylbenzenesulfonyl chloride as described in the synthetic METHOD B to give a yellow solid (9.4 mg) with purity >90%: MS (pos) m/z 439.1, 441.1; HRS m/z 437.8875 (calc. of monoisotopic mass for $C_{14}H_9Cl_3N_2O_2S_3$ gives 437.8892).

EXAMPLE 60 [311A]

2,4-Dichloro-N-[4-(2-chlorophenyl)-1,3-thiazol-2-yl]-6-methylbenzenesulfonamide

The title compound was prepared from 4-(2-chlorophenyl)-1,3-thiazol-2-amine and 2,4-dichloro-6-methylbenzenesulfonyl chloride as described in the synthetic METHOD B to give a white solid (40.3 mg) with purity >90%. MS (pos) m/z 435.0, 437.0.

EXAMPLE 61 [312A]

Ethyl 2-[([1,1'-biphenyl]-4-ylsulfonyl)amino]-4-phenyl-1,3-thiazole-5-carboxylate The title compound was prepared from 2-amino-4-phenylthiazole-5-carboxylate and 4-biphenylsulfonyl chloride as described in the synthetic METHOD B to give a white solid (21.7 mg) with purity >90%. LCMS (pos) m/z 465.2.

EXAMPLE 62 [313A]

3-Chloro-N-[4-(4-methoxyphenyl)-1,3-thiazol-2-yl]-2-methylbenzenesulfonamide

The title compound was prepared from 4-(4-methoxyphenyl)-thiazol-2-ylamine and 3-chloro-2-methylbenzenesulfonyl chloride as described in the synthetic METHOD B to give a white solid (58.0 mg) with purity >90%. MS (pos) m/z 395.2.

EXAMPLE 63 [313B]

N-[4-(2-{[(4-Bromo-2,5-idfluorophenyl)sulfonyl]amino}-1,3-thiazol-4-yl)phenyl]acetamide The title compound was prepared N-[4-(2-amino-1,3-thiazol-4-yl)phenyl]acetamide (63 mg) and 4-bromo-2,5-difluorobenzenesulfonyl chloride (79 mg) as described in the synthetic METHOD B to give a white-yellow solid (6.2 mg) with purity >90%: MS (pos) m/z 488.3, 490.3.

EXAMPLE 64 [313C]

2,3,4-Trichloro-N-[4-(2-chlorophenyl)-1,3-thiazol-2-yl]benzenesulfonamide

The title compound was prepared from 4-(2-chlorophenyl)-1,3-thiazol-2-amine (57 mg) and 2,3,4-trichlorobenzenesulfonyl chloride (76 mg) as described in the synthetic METHOD B to give a white solid (64.8 mg) with purity >90%: MS (pos) m/z 453.3, 455.3, 457.2.

EXAMPLE 65 [313D]

2,4,5-Trichloro-N-[4-(3-chloro-2-thienyl)-1,3-thiazol-2-yl]benzenesulfonamide

The title compound was prepared from 4-(3-chloro-2-thienyl)-1,3-thiazol-2-amine (59 mg) and 2,4,5-trichlorobenzenesulfonyl chloride (76 mg) as described in the synthetic METHOD B to give a white solid (9.2 mg) with purity >90%: MS (pos) m/z 459.2, 461.2, 463.2.

EXAMPLE 66 [313E]

2,3,4-Trichloro-N-[4-(3-chloro-2-thienyl)-1,3-thiazol-2-yl]benzenesulfonamide

The title compound was prepared from 4-(3-chloro-2-thienyl)-1,3-thiazol-2-amine (59 mg) and 2,3,4-trichlorobenzenesulfonyl chloride (76 mg) as described in the synthetic METHOD B to give a white solid (5.0 mg) with purity >90%: MS (pos) m/z 459.2, 461.2, 463.2.

EXAMPLE 67 [313F]

4-Bromo-N-[4-(3-chloro-2-thienyl)-1,3-thiazol-2-yl]-2,5-difluorobenzenesulfonamide The title compound was prepared 4-(3-chloro-2-thienyl)-1,3-thiazol-2-amine (59 mg) and 4-bromo-2,5-difluorobenzenesulfonyl chloride (79 mg) as described in the synthetic METHOD B to give a white solid (22.3 mg) with purity >90%: MS (pos) m/z 471.2, 473.2.

EXAMPLE 68 [313G]

4,5-Dichloro-N-(7-methoxy-4,5-dihydronaphtho[1,2-d][1,3]thiazol-2-yl)-2-thiophenesulfonamide The title compound was prepared from 7-methoxy-4,5-dihydronaphtho(1,2-D)(1,3)thiazol-2-amine hydrobromide (85 mg) and 2,3-dichlorothiophene-5-sulfonyl chloride (68 mg) as described in the synthetic METHOD B to give a white solid (16.4 mg) with purity >90%: MS (pos) m/z 447.3, 449.3.

EXAMPLE 69 [3131H]

4,5-Dichloro-N-[4-(2-chlorophenyl)-1,3-thiazol-2-yl]-2-thiophenesulfonamide

The title compound was prepared from 4-(2-chlorophenyl)-1,3-thiazol-2-amine (57 mg) and 2,3-dichlorothiophene-5-sulfonyl chloride (68 mg) as described in the synthetic METHOD B to give a white solid (56.6 mg) with purity >90%: MS (pos) m/z 425.3, 427.3; HRMS m/z 423.8737 (calc. of monoisotopic mass for $C_{13}H_7Cl_3N_2O_2S_3$ gives 423.8735).

EXAMPLE 70 [313I]

N-[4-(2-{[(2,4,5-Trichlorophenyl)sulfonyl]amino}-1,3-thiazol-4-yl)pbenyl]acetamide The title compound was prepared from N-[4-(2-amino-1,3-thiazol-4-yl)phenyl]acetamide (63 mg) and 2,4,5-trichlorobenzenesulfonyl chloride (76 mg) as described in the synthetic METHOD B to give a white-yellow solid (5,0 mg) with purity >90%: MS (pos) m/z 476.3. 478.3.

EXAMPLE 71 [313J]

2,3,4-Trichloro-N-(7-methoxy-4,5-dihydronaphtho[1,2-d][1,3]thiazol-2-yl)benzenesulfonamide The title compound was prepared from 7-methoxy-4,5-dihydronaphtho(1,2-D)(1,3)thiazol-2-amine hydrobromide (85 mg) and 2,3,4-trichlorobenzenesulfonyl chloride (76 ng) as described in the synthetic METHOD B to give a white solid (13.1 mg) with purity >90%: MS (pos) m/z 475.3, 477.3

EXAMPLE 72 [313K]

4-Bromo-5-chloro-N-[4-(3-chloro-2-thienyl)-1,3-thiazol-2-yl]-2-thiophenesulfonamide The title compound was prepared from 4-(3-chloro-2-thienyl)-1,3-thiazol-2-amine (59 mg) and 4-bromo-5-chlorothiophene-2-sulfonyl chloride (80 mg) as described in the synthetic METHOD B to give a white solid (34.2 mg) with purity >90%: MS (pos) m/z 457.1, 477.1, 479.1.

EXAMPLE 73 [313L]

3-Bromo-5-chloro-N-(7-methoxy4,5-dihydronaphtho[1,2-d][1,3]thiazol-2-yl)-2-thiophenesulfonamide The title compound was prepared 7-methoxy-4,5-dihydronaphtho(1,2-D)(1,3)thiazol-2-amine hydrobromide (85 mg) and 3-bromo-5-chlorothiophene-2-sulfonyl chloride (80 mg) as described in the synthetic METHOD B to give a white solid (17.8 mg) with purity >80%: MS (pos) m/z 491.3, 493.3.

EXAMPLE 74 [313M]

3-Bromo-5-chloro-N-[4-chlorophenyl)-1,3-thiazol-2-yl]-2-thiophenesulfonamide

The title compound was prepared from 4-(2-chlorophenyl)-1,3-thiazol-2-amine (57 mg) and 3-bromo-5-chlorothiophene-2-sulfonyl chloride (80 mg) as described in the synthetic METHOD B to give a white solid (43.7 mg) with purity >90%: MS (pos) m/z 469.2, 471.2, 473.2.

EXAMPLE 75 [313N]

N-[4-(2-{[(2,6-Dichlorophenyl)sulfonyl]amino}-1,3-thiazol-4-yl)phenyl]acetamide

The title compound was prepared from N-[4-(2-amino-1,3-thiazol-4-yl)phenyl]acetamide (63 mg) and 2,6-dichlorobenzenesulfonyl chloride (66 mg) as described in the synthetic METHOD B to give a white solid (5.6 mg) with purity >80%: MS (pos) m/z 442.2, 444.4.

EXAMPLE 76 [313O]

2,6-Dichloro-N-[4-(3-chloro-2-thienyl)-1,3-thiazol-2-yl]benzenesulfonamide

The title compound was prepared from 4-(3-chloro-2-thienyl)-1,3-thiazol-2-amine (59 mg) and 2,6-dichlorobenzenesulfonyl chloride (66 mg) as descrbed in the synthetic METHOD B to give a yellow solid (34.5 mg) with purity >90%: MS (pos) m/z 425.3, 427.3; HRMS m/z 423.8730 (calc. of monoisotopic mass for $C_{13} H_7 Cl_3 N_2 O_2 S_3$ gives 423.8735).

EXAMPLE 77 [313P]

2,4,6-Trichloro-N-(7,8-dimethoxy-4,5-dihydronaphtho[1,2-d][1,3]thiazol-2-yl)benzenesulfonamide The title compound was prepared from 7,8-dimethoxy-4,5-dihydronaphtho[1,2-d][1,3]thiazol-2-amine (100 mg, synthesized according to METHOD I from 6,7-dimethoxytetralone) and 2,4,6-trichlorobenzenesulfonyl chloride (213 mg) as described in the synthetic METHOD A to give a yellow powder (6.5 mg) with a purity of 86%: MS-ES (neg) m/z 505.1

EXAMPLE 78 [313Q]

2,3,4-Trichloro-N-{4-[2-chloro-4-(4-chlorophenoxy)phenyl]-1,3-thiazol-2-yl)benzenesulfonamide The title compound was prepared from 4-[2-chloro-4-(4-chlorophenoxy)phenyl]-1,3-thiazol-2-amine (91 mg) and 2,3,4-trichlorobenzenesulfonyl chloride (76 mg) as described in the synthetic METHOD B to give a white solid (49.2 mg) with purity >90%: MS (pos) m/z 579.1, 581.1, 583.1; MS (neg) m/z 577.5, 579.5, 581.5.

EXAMPLE 79 [313R]

2,3,4-Trichloro-N-{4-[2,6-dichloro-(trifluoromethyl)phenyl]-1,3-thiazol-2-yl)bezenesulfonamide The title compound was prepared from 4-[2,6-dichloro-4-(trifluoromethyl)phenyl]-1,3-thiazol-2-amine (85 mg) and 2,3,4-trichlorobenzenesulfonyl chloride (76 mg) as described in the synthetic METHOD B to give a white solid (94.0 mg) with purity >90%: MS (pos) m/z 555.1, 557.1, 559.1; MS (neg) m/z 553.4, 555.4, 557.4; HRMS m/z 553.8262 (calc. of monoisotopic mass for $C_{16} H_6 Cl_5 F_3 N_2 O_2 S_2$ gives 553.8265).

EXAMPLE 80 [313S]

N-[4-(2-Chloro-6-fluorophenyl)-1,3-thiazol-2-yl]-4-propylbenzenesulfonamide

The title compound was prepared from 4-(2-chloro-6-fluorophenyl)-1,3-thiazol-2-amine (62 mg) and 4-n-propylbenzenesulfonyl chloride (59 mg) as descibed in the synthetic METHOD B to give a white solid (30.7 mg) with purity >90%: MS (pos) m/z 411.3, 413.3; MS (neg) m/z 409.5, 411.5.

EXAMPLE 81 [313T]

4-Bromo-N-{4-[2-chloro-4-(4-chlorophenoxy)phenyl]-1,3-thiazol-2-yl}-2,5-difluorobenzenesulfonamide The title compound was prepared 4-[2-chloro-4-(4-chlorophenoxy)phenyl]-1,3-thiazol-2-amine (91 mg) and 4-bromo-2,5-difluorobenzenesulfonyl chloride (79 mg) as described in the synthetic METHOD B to give a white solid (46.9 mg) with purity >90%: MS (neg) m/z 589.5, 591.5, 593.5; HRMS m/z 589.8745 (calc. of monoisotopic mass for $C_{21} H_{11} Br Cl_2 F_2 N_2 O_3 S_2$ gives 589.8740).

EXAMPLE 82 [313U]

4-Bromo-N-{4-[2,6-dichloro-4-(trifluoromethyl)phenyl]-1,3-thiazol-2-yl}-2,5-difluorobenzenesulfonamide The title compound was prepared 4-[2,6-dichloro-4-(trifluoromethyl)phenyl]-1,3-thiazol-2-amine (85 mg) and 4-bromo-2,5-difluorobenzenesulfonyl chloride (79 mg) as described in the synthetic METHOD B to give a white solid (38.2 mg) with purity >90%: MS (pos) m/z 567.2, 569.2, 571.2; MS (neg) m/z 565.5, 567.5, 569.5.

EXAMPLE 83 [313V]

4,5-Dichloro-N-[4-(2-chloro-6-fluorophenyl)-1,3-thiazol-2-yl]-2-thiophenesulfonamide The title compound was 4-(2-chloro-6-fluorophenyl)-1,3-thiazol-2-amine (62 mg) and 2,3-dichlorothiophene-5-sulfonyl chloride (68 mg) as descnbed in the synthetic METHOD B to give a white solid (46.6 mg) with purity >90%: MS (pos) m/z 443.2, 445.2, 447.2; MS (neg) m/z 441.2, 443.2, 445.2; HRMS m/z 441.8657 (calc. of monoisotopic mass for $C_{13} H_{16} Cl_3 FN_2 O_2 S_3$ gives 441.8641).

EXAMPLE 84 [313W]

4-Bromo-5-chloro-N-{4-[2-chloro-4-(4-chlorophenoxy) phenyl]-1,3-thiazol-2-yl}-2-thiophenesulfonamide The title compound 4-[2-chloro-4-(4-chlorophenoxy) phenyl]-1,3-thiazol-2-amine (91 mg) and 4-bromo-5-chlorothiophene-2-sulfonyl chloride (80 mg) as described in the synthetic METHOD B to give a white solid (44.4 mg) with purity >90%: MS (pos) m/z 595.3, 597.3, 599.3; MS (neg) m/z 593.2, 595.2, 597.2.

EXAMPLE 85 [313X]

4-Bromo-5-chloro-N-{4-[2,6-dichloro-4-(trifluoromethy)lphenyl]-1,3-thiazol-2-yl}-2-thiophenesulfonamide The title compound 4-[2,6-dichloro-4-(trifluoromethyl)phenyl]-1,3-thiazol-2-amine (85 mg) and 4-bromo-5-chlorothiophene-2-sulfonyl chloride (80 mg) as described in the synthetic METHOD B to give a white solid (65.3 mg) with purity >90%: MS (pos) m/z 571.2, 573.2, 575.2; MS (neg) m/z 569.1, 571.1, 573.3; HRMS m/z 569.7690 (calc. of monoisotopic mass for $C_{14} H_5 Br Cl_3 F_3 N_2 O_2 S_3$ gives 569.7714).

EXAMPLE 86 [313Y]

2,4-Dichloro-N-[4-(2-chloro-6-fluorophenyl)-1,3-thiazol-2-yl]-6-methylbenzenesulfonamide The title compound was 4-(2-chloro-6-fluorophenyl)-1,3-thiazol-2-amine (62 mg) and 2,4-dichloro-6-methylbenzenesulfonyl chloride (70 mg) as described in the synthetic METHOD B to give a white solid (41.6 mg) with purity >90%: MS (pos) m/z 451.3, 453.3, 455.3; MS (neg) m/z 449.3, 451.3, 453.3.

EXAMPLE 87 [313Z]

2,4,6-Trichloro-N-{4-[2,6-dichloro-4-trifluoromethyl) phenyl]-1,3-thiazol-2-yl}benzenesulfonamide The title compound was 4-[2,6-dichloro-4-(trifluoromethyl)phenyl]-1,3-thiazol-2-amine (85 mg) and 2,4,6-trichlorobenzenesulfonyl chloride (76 mg) as described in the synthetic METHOD B to give a white solid (44.1 mg) with purity >90%: MS (pos) m/z 555.3, 557.3, 559.3; MS (neg) m/z 553.2, 555.2, 557.2.

EXAMPLE 88 [313Z]

4-Bromo-N-[4-(2-chloro-6-fluorophenyl)-1,3-thiazol-2-yl]-2-methylbenzenesulfonamide The title compound was was 4-(2-chloro-6-fluorophenyl)-1,3-thiazol-2-amine (62 mg) and 4-bromo-2-methylbenzenesulfonyl chloride (73 mg) as described in the synthetic METHOD B to give a white solid (18.0 mg) with purity >90%: MS (pos) m/z 461.3, 463.3, 465.4; MS (neg) m/z 459.3, 461.3, 463.3.

EXAMPLE 89 [313ZB]

2,4,6-Trichloro-N-{4-[2-chloro-4-(4-chlorophenoxy) phenyl]-1,3-thiazol-2-yl}benzenesulfonamide The title compound was 4-[2-chloro-4-(4-chlorophenoxy) phenyl]-1,3-thiazol-2-amine (91 mg) and 2,4,6-trichlorobenzenesulfonyl chloride (76 mg) as described in the synthetic METHOD B to give a white solid (18.8 mg) with purity >90%: MS (pos) m/z 578.9, 580.9, 582.9.

EXAMPLE 90 [313ZC]

N-[4-(2-{[(4-Bromo-5-chloro-2-thienyl)sulfonyl]amino}-1,3-thiazol-4-yl)phenyl]acetamide The title compound was prepared N-[4-(2-amino-1,3-thiazol-4-yl)phenyl}acetamide (63 mg) and 4-bromo-5-chlorothiophene-2-sulfonyl chloride (80 mg) as described in the synthetic METHOD B to give a white solid (11.7 mg) with purity >80%: MS (pos) m/z 491.9, 493.9.

EXAMPLE 91 [313ZD]

N-(4,5-Dihydrothieno[3,2-e][1,3]benzothiazol-2-yl)benzenesulfonamide

The title compound was prepared from 4,5-dihydrothieno[3,2-e][1,3]benzothiazol-2-amine (106 mg, synthesized according to METHOD I from 4-keto-4,5,6,7-tetrahydrothianaphthene) and benzenesulfonyl chloride (93 mg) as described in the synthetic METHOD A to give a white solid (13 mg) with a purity >90%: MS-ES (neg) m/z 347.2.

EXAMPLE 92 [313ZE]

3,4-Dichloro-N-(4,5-dihydrothieno[3,2-e][1,3]benzothiazol-2-yl)benzenesulfonamide The title compound was prepared from 4,5-dihyrothieno[3,2-e][1,3]benzothiazol-2-amine (107 mg, synthesized according to METHOD I from 4-keto-4,5,6,7-tetrahydrothianaphthene) and 3,4-dichlorobenzenesulfonyl chloride (127 mg) as described in the synthetic METHOD A to give a white powder (62 mg) with a purity >90%: MS-ES (neg) m/z 417.2.

EXAMPLE 93 [313ZF]

3-Chloro-N-(4,5-dihydrothieno[3,2-e][1,3]benzothiazol-2-yl)-2-methylbenzenesulfonamide The title compound was prepared from 4,5-dihydrothieno[3,2-e][1,3]benzothiazol-2-amine (106 mg, synthesized according to METHOD I from 4-keto-4,5,6,7-tetrahydrothianaphthene) and 3-chloro-2-methylbenzenesulfonyl chloride (114mg) as described in the synthetic METHOD A to give a white powder (36 mg) with a purity >90%: MS-ES (neg) m/z 395.2.

EXAMPLE 94 [313ZG]

2,4,6-Trichloro-N-(4,5-dihydrothieno[3,2-e][1,3]benzothiazol-2-yl)benzenesulfonamide The title compound was prepared from 4,5-dihydrothieno[3,2-e][1,3]benzothiazol-2-amine (106 mg, synthesized according to METHOD I from 4-keto-4,5,6,7-tetrahydrothianaphthene) and 2,4,6-trichlorobenenesulfonyl chloride (141 mg) as described in the synthetic METHOD A to give a white powder (12 mg) with a purity >90%: MS-ES (neg) m/z 451.2.

EXAMPLE 95 [313ZH]

N-(4,5-Dihydrothieno[3,2-e[]1,3]benzothiazol-2-yl)(1,1'-biphenyl]-4-sulfonamide

The title compound was prepared from 4,5-dihydrothieno[3,2-e][1,3]benzothiazol-2-amine (109 mg, synthesized according to METHOD I from 4-keto-4,5,6,7-tetrahydrothianaphthene) and 4-biphenylsulfonyl chloride (130 mg) as described in the synthetic METHOD A to give a white powder (12 mg) with a purity >90%: MS-ES (neg) m/z 423.3.

EXAMPLE 96 [313ZI]

2,4-Dichloro-N-(4,5-dihydrothieno[3,2-e][1,3]benzothiazol-2-yl)-6-methylbenzenesulfonamide The title compound was prepared from 4,5-dihydrothieno[3,2-e][1,3]benzothiazl-2-amine (105 mg, synthesized according to METHOD I from 4-keto-4,5,6,7-tetrahydrothianaphthene) and 2,4-dichloro-6-methylbenzenesulfonyl chloride (132 mg) as desribed in the synthetic METHOD A to give a white powder (21 mg) with a purity >90%: MS-ES (neg) m/z 431.2.

EXAMPLE 97 [313ZJ]

N-(4,5-Dihydrothieno[3,2-e][1,3]benzothiazol-2-yl)-4-propylbenzenesulfonamide

The title compound was prepared from 4,5-dihydrothieno[3,2-e][1,3]benzothiazol-2-amine (105 mg, synthesized according to METHOD I from 4-keto-4,5,6,7-tetrahydrothianaphthene) and 4-n-propylbenzenesulfonyl chloride (111 mg) as described in the synthetic METHOD A to give a white powder (18 mg) with a purity >90%: MS-ES (neg) m/z 389.3.

EXAMPLE 98 [313ZK]

3-Chloro-N-[6-chloro-8-(methylsulfonyl)-4,5-dihydrothieno[3,4-e][1,3]benzothiazol-2-yl]-2-methylbenzenesulfonamide The title compound was prepared from 6-chloro-8-(methylsulfonyl)-4,5-dihydrothieno[3,4-e][1,3]benzothiazol-2-amine (61 mg, synthesized according to METHOD I from 1-chloro-3-methylsulfonyl)-4,5,6,7-tetrahydrobenzo-[c]thiophen-4-one) and 3-chloro-2-methylbenzesulfonyl chloride (47 mg) as described in the synthetic METHOD A to give a beige solid (24 mg) with a purity >90%: MS-ES (pos) m/z 509.1.

EXAMPLE 99 [313ZL]

N-[6-Chloro-8-(methylsulfonyl)-4,5-dihydrothieno[3,4-e][1,3]benzothiazol-2-yl]-4-propylbenzenesulfonamide The title compound was prepared from 6-chloro-8-(methylsulfonyl)-4,5-dihydrothieno[3,4-e][1,3]benzothiazol-2-amine (61 mg, synthesized according to METHOD I from 1-chloro-3-(methylsulfonyl)-4,5,6,7-tetrahydrobenzo-[c]thiophen-4-one) and 4-n-propylbenzenesulfonyl chloride (46 mg) as described in the synthetic METHOD A to give a white powder (18 mg) with a purity of 90%: MS-ES (pos) m/z 501.2.

EXAMPLE 100 [313ZM]

2,4-Dichloro-N-[6-chloro-8-(methylsulfonyl)-4,5-dihydrothieno[3,4-e][1,3]benzothiazol-2-yl]-6-methylbenzenesulfonamide The title compound was prepared from 6-chloro-8-(methylsulfonyl)-4,5-dihydrothieno[3,4-e][1,3]benzothiazol-2-amine (61 mg, synthesized according to METHOD I from 1-chloro-3-(methylsulfonyl)-4,5,6,7-tetrahydrobenzo-[c]thiophen-4-one) and 2,4-dichloro-6-methylbenzenesulfonyl chloride (54 mg) as described in the synthetic METHOD A to give a white solid (5.9 mg) with a purity >90%: MS-ES (pos) m/z 543.1.

EXAMPLE 101 [313ZN]

N-[6-Chloro-8-(methylsulfonyl)-4,5-dihydrothieno[3,4-e][1,3]benzothiazol-2-yl][1,1'-biphenyl]-4-sulfonamide The title compound was prepared from 6-chloro-8-(methylsulfonyl)4,5-dihydrothieno[3,4-e][1,3]benzothiazol-2-amine (61 mg, synesized according to METHOD I from 1-chloro-3-(methylsulfonyl)-4,5,6,7-tetrahydrobenzo-[c]thiophen-4-one) and 4-biphenylsulfonyl chloride (52 mg) as described in the synthetic METHOD A to give a beige solid (5.9 mg) with a purity >90%: MS-ES (neg) m/z 535.2.

EXAMPLE 102 [313ZO]

N-{2-[(Phenylsulfonyl)amino]-4,5-dihydronaphtho[1,2-d][1,3]thiazol-6-yl}acetamide The title compound was prepared from 2-amino-4,5-dihydronaphtho[1,2-d][1,3]thiazol-6-yl}acetamide (100 mg, synthesized according to METHOD I from 6-acetamidotetralone) and benzenesulfonyl chloride (81 mg) as described in the synthetic METHOD A to give a cream powder (4.8 mg) with a purity >90%: MS-ES (neg) m/z 398.4.

EXAMPLE 103 [313ZP]

N-(2-{[(3-Chloro-2-methylphenyl)sulfonyl]amino}naphtho[1,2-d][1,3]thiazol-6-yl)acetamide The title compound was prepared from 2-amino-4,5-dihydronaphtho[1,2-d][1,3]thiazol-6-yl}acetamide (100 mg synthesized according to METHOD I from 6-acetamidotetralone) and 3-chloro-2-methylbenzenesulfonyl chloride (129 mg) as described in the synthetic METHOD A to give a cream powder (1.1 mg) with a purity of 87%: MS-ES (neg) m/z 444.3.

EXAMPLE 104 [313ZQ]

N-(2-{[(4-Propylphenyl)sulfonyl]amino}-4,5-dihydronaphtho[1,2-d][1,3]thiazol-6-yl)acetamide The title compound was prepared from 2-amino-4,5-dihydronaphtho[1,2-d][1,3]thiazol-6-yl}acetamide (100 mg, synthesized according to METHOD I from 6-acetamidotetralone) and 4-n-propylbenzenesulfonyl chloride (101 mg) as described in the synthetic METHOD A to give a cream powder (18 mg) with a purity >90%: MS-ES (neg) m/z 440.4.

EXAMPLE 105 [313ZR]

N-(8-Nitro-4,5-dihydronaphtho[1,2-d][1,3]thiazol-2-yl)4-propylbenzenesulfonamide The title compound was prepared from 8-nitro-4,5-dihydronaphtho[1,2-d][1,3]thiazol-2-amine (100 mg, synthesized according to METHOD I from 7-nitrotetralone) and 4-n-propylbenzenesulfonyl chloride (106 mg) as described in the synthetic METHOD A to give a yellow powder (3.5 mg) with a purity of 87%: MS-ES (neg) m/z 428.4.

EXAMPLE 106 [313ZS]

N-(8-Nitro-4,5-dihydronaphtho[1,2-d][1,3]thiazol-2-yl)benzenesulfonamide

The title compound was prepared from 8-nitro-4,5-dihydronaphtho[1,2-d][1,3]thiazol-2-amine (100 mg, synthesized according to METHOD I from 7-nitrotetralone) and benzenesulfonyl chloride (85 mg) as described in the synthetic METHOD A to give a yellow powder (12 mg) with a purity of >90%: MS-ES (neg) m/z 386.3.

EXAMPLE 107 [313ZT]

N-(8-Nitro-4,5-dihydronaphtho[1,2-d][1,3]thiazol-2-yl)[1,1'-biphenyl]-4-sulfonamide The title compound was prepared from 8nitro-4,5-dihydronaphtho[1,2-d][1,3]thiazol-2-amine (100 mg, synthesized according to METHOD I from 7-nitrotetralone) and 4-biphenylsulfonyl chloride (122 mg) as described in the synetic METHOD A to give a yellow powder (4.4 mg) with a purity of >90%: MS-ES (neg) m/z 462.4.

Various embodiments of the present invention have been described above but a person skilled in the art realizes further minor alterations which would fall into the scope of the present invention. The breadth and scope of the present invention should not be limited by any of the above-described exemplary embodiments, but should be defined only in accordance with the following claims and their equivalents.

The invention claimed is:

1. A compound of the formula (I):

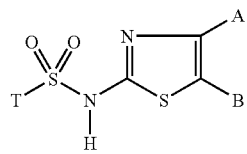

wherein

T is selected from thienyl substituted with one or more of bromo, chloro; phenyl substituted as follows:
   a) either T is phenyl, wherein the phenyl is substituted with one or more phenyl;
   b) T is phenyl substituted with chloro in position 3 and methyl in position 2;
   c) T is phenyl substituted with chloro in position 2 and 4, and methyl in position 6;
   d) T is phenyl substituted with bromo in position 4 and fluoro in position 2 and 5;
   e) T is phenyl substituted with chloro in position 2, 3, and 4;
   f) T is phenyl substituted with chloro in position 2, 4, and 5;
   g) T is phenyl substituted with bromo in position 4 and methyl in position 2;
   h) T is phenyl substituted with chloro in position 2 and 6;
   i) T is phenyl substituted with chloro in position 2, 4, and 6; or
   j) T is phenyl substituted with bromo in position 4 and chloro in position 5;

A is selected from an aryl ring or heteroaryl ring, which can further be optionally substituted in one or more positions independently of each other by hydrogen, $C_{1-6}$-alkyl, halogenated $C_{1-6}$-alkyl, halogen, $C_{1-6}$-alkoxy, nitro, $C_{1-6}$-alkoxycarbonyl, $C_{1-6}$-alkylsulfonyl, acetylamino or aryloxy, wherein the aryloxy can further be optionally substituted in one or more positions independently of each other by hydrogen and halogen;

B is selected from hydrogen and $C_{1-6}$-alkoxycarbonyl or is linked to A to give a cyclic structure selected from the group consisting of:

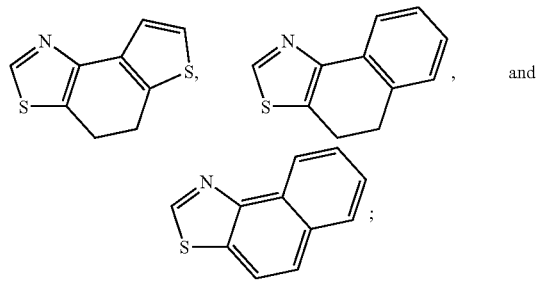

as well as pharmaceutically acceptable salts, hydrates and solvates thereof.

2. A compound according to claim 1, wherein
   A is selected from 1-benzothien-3-yl, 3-(2,5-dimethylfuryl), pyridinyl; thienyl optionally substituted with one or more of chloro, methylsulfonyl; phenyl optionally substituted with one or more of ethoxycarbonyl, nitro, fluoro, methyl, methoxy, acetylamino, chloro, 4-chlorophenoxy, trifluoromethyl;
   B is selected from hydrogen, carbethoxy or is linked to A to give a cyclic structure selected from the croup consisting of:

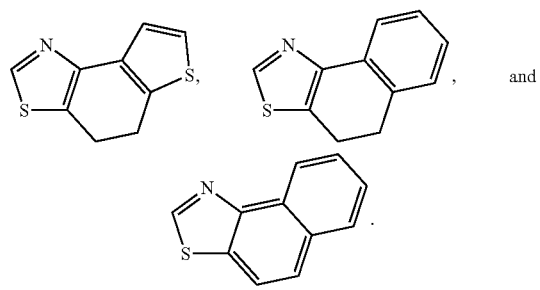

3. A compound selected from the group consisting of:
Ethyl 2-{[(3-chloro-2-methylphenyl)sulfonyl]amino)}-4-phenyl-1,3-thiazole-5-carboxylate,
3-Chloro-2-methyl-N-[4-(3-nitrophenyl)-1,3-thiazol-2-yl]benzenesulfonamide,
3-Chloro-2-methyl-N-[4-phenyl)-1,3-thiazol-2-yl]benzenesulfonamide,
3-Chloro-N-[4-(4-fluoro-3-methylphenyl)-1,3-thiazol-2-yl]-2-methylbenzenesulfonamide,
2,4,6-Trichloro-N-[4-(3-nitrophenyl)-1,3-thiazol-2-yl]benzenesulfonamide,
2,4,6-Trichloro-N-(4-phenyl-1,3-thiazol-2-yl)benzenesulfonamide,
2,4,6-Trichloro-N-[4-(4-fluoro-3-methylphenyl)-1,3-thiazol-2-yl]benzenesulfonamide,
2,4,6-Trichloro-N-[4-(4-methoxyphenyl)-1,3-thiazol-2-yl]benzenesulfonamide,
N-[4-(3-nitrophenyl)-1,3-thiazol-2-yl][1,1'-biphenyl]-4-sulfonamide,
N-(4-phenyl-1,3-thiazol-2-yl)[1,1'-biphenyl]-4-sulfonamide,
N-[4-(4-Fluoro-3-methylphenyl)-1,3-thiazol-2-yl][1,1'-biphenyl]-4-sulfonamide,
N-[4-(4-Methoxyphenyl)-1,3-thiazol-2-yl][1,1'-biphenyl]-4-sulfonamide, 2,4-Dichloro-6-methyl-N-[4-(3-nitrophenyl)-1,3-thiazol-2-yl]benzenesulfonamide, 2,4-Dichloro-6-methyl-N-(4-phenyl)-1,3-thiazol-2-yl]benzenesulfonamide, 2,4-Dichloro-N-[4-(4-fluoro-3-methylphenyl)-1,3-thiazol-2-yl]-6-methylbenzenesulfonamide, 2,4-Dichloro-N-[4-(4-methoxyphenyl)-1,3-thiazol-2-yl]-6-methylbenzenesulfonamide, N-[4-(2-{[(3-chloro-2-methylphenyl)sulfonyl]amino}-1,3-thiazol-4-yl)phenyl]acetamide, 3-Chloro-2-methyl-N-[4-(3-pyridinyl)-1,3-thiazol-2-yl]benzenesulfonamide, 3-Chloro-N-[4-(2-chloro-5-nitrophenyl)-1,3-thiazol-2-yl]-2-methylbenzenesulfonamide, 3-Chloro-N-(7-methoxy-4,5-dihydronaphtho[1,2-d][1,3]thiazol-2-yl)-2-methylbenzenesulfonamide, 3-Chloro-N-(4-(5-chloro-2-thienyl)1-3-thiazol-2-yl]-2-methylbenzenesulfonamide, 3-Chloro-N-[4-(2-chlorophenyl)-1,3-thiazol-2-yl]-2-methylbenzenesulfonamide, N-[4-(2-{[(2,4,6-trichlorophenyl)sulfonyl]amino}-1,3-thiazol-4-yl)phenyl]acetamide, 2,4,6-Trichloro-N-[4-(3-pyridinyl)-1,3-thiazol-2-yl]benzenesulfonamide, 2,4,6-Trichloro-N-[4-(2-chloro-5-nitrophenyl)-1,3-thiazol-2-yl]benzenesulfonamide, 2,4,6-Trichloro-N-[7-methoxy-4,5-dihydronaphtho[1,2-d][1,3]thiazol-2-yl]benzenesulfonamide, 2,4,6-Trichloro-N-[4-(5-chloro-2-thienyl)-1,3-thiazol-2-yl]benzenesulfonamide, 2,4,6-Trichloro-N-[4-(2-chlorophenyl)-1,3-thiazol-2-yl]benzenesulfonamide, N-[4-{2[([1,1'-biphenyl]-4-ylsulfonyl]amino]-1,3-thiazol-4-yl)phenyl]acetamide, N-[4-(3-pyridinyl)-1,3-thiazol-2-yl][1,1'-biphenyl]-4-sulfonamide, N-[4-(2-chloro-5-nitrophenyl)-1,3-thiazol-2-yl][1,1'-biphenyl]-4-sulfonamide, N-(7-methoxy-4,5-dihydronaphtho[1,2-d][1,3-thiazol-2-yl][1,1'-biphenyl]-4-sulfonamide, N-[4-(5-chloro-2-thienyl)-1,3-thiazol-2-yl][1,1'-biphenyl]-4-sulfonamide, N-[4-(2-chlorophenyl)-1,3-thiazol-2-yl][1,1'-biphenyl]-4-sulfonamide, N-[4-(2-{[(2,4-dichloro-6-methylphenyl)sulfonyl]amino)-1,3-thiazol-4-yl) phenyl]acetamide, 2,4-Dichloro-6-methyl-N-[4-(3-pyridinyl)1,3-thiazol-2-yl]benzenesulfonamide, 2,4-Dichloro-N-[4-(2-chloro-5-nitrophenyl)-1,3-thiazol-2-yl]-6-methylbenzenesulfonamide, 2,4-Dichloro-N-(7-methoxy-4,5-dihydronaphtho[1,2-d][1,3]thiazol-2-yl)-6-methylbenzenesulfonamide, 2,4-Dichloro-N-[4-(5-chloro-2-thienyl)-1,3-thiazol-2-yl]-6-methylbenzenesulfonamide, 2,4-Dichloro-N-[4-(2,5-dimethyl-3-furyl)-1,3-thiazol-2-yl]-6-methylbenzenesulfonamide, N-[4-(1-benzothien-3-yl)-1,3-thiazol-2-yl]-2,4-dichloro-6-methylbenzenesulfonamide, 3-Chloro-N-[4-(3-chloro-2-thienyl)-1,3-thiazol-2-yl]-2-methylbenzenesulfonamide, 2,4,6-Trichloro-N-[4-(3-chloro-2-thienyl)-1,3-thiazol-2-yl]benzenesulfonamide, 2,4-Dichloro-N-[4-(3-chloro-2-thienyl)-1,3-thiazol-2-yl]-6-methylbenzenesulfonamide, 2,4-Dichloro-N-[4-(2-chlorophenyl)-1,3-thiazol-2-yl]-6-methylbenzenesulfonamide, Ethyl 2-[{[1,1'-biphenyl]-4-ylsulfonyl)amino]-4-phenyl-1,3-thiazole-5-carboxylate, 3-Chloro-N-[4-(4-methoxyphenyl)-1,3-thiazol-2-yl]-2-methylbenzenesulfonamide, N-[4-(2-{[(4-Bromo-2,5-difluorophenyl)sulfonyl]amino}-1,3-thiazol-4-yl) phenyl]acetainide, 2,3,4-Trichloro-N-[4-(2-chlorophenyl)-1,3-thiazol-2-yl]benzenesulfonamide, 2,4,5-Trichloro-N-[4-(3-chloro-2-thienyl)-1,3-thiazol-2-yl]benzenesulfonamide, 2,3,4-Trichloro-N-[4-(3-chloro-2-thienyl)-1,3-thiazol-2-yl]benzenesulfonamide, 4-Bromo-N-[4-(3-chloro-2-thienyl)-1,3-thiazol-2-yl]-2,5-difluorobenzenesulfonamide, 4,5-Dichloro-N-(7-methoxy-4,5-dihydronaphtho[1,2-d][1,3]thiazol-2-yl)-2-thiophenesulfonamide, 4,5-Dichloro-N-[4-(2-chlorophenyl)-1,3-thiazol-2-yl]-2-thiophenesulfonamide, N-[4-(2-{[2,4,5-Trichlorophenyl]sulfonyl}amino)-1,3-thiazol-4-yl]phenyl]acetamide, 2,3,4-Trichloro-N-(7-methoxy-4,5-dihydronaphtho[1,2-d][1,3]thiazol-2-yl) benzenesulfonamide, 4-Bromo-5-chloro-N-[4-(3-chloro-2-thienyl)-1,3-thiazol-2-yl]-2-thiophenesulfonamide, 3-Bromo-5-chloro-N-(7-methoxy-4,5-dihydronaphtho[1,2-d][1,3]thiazol-2-yl)-2-thiophenesulfonamide, 3-Bromo-5-chloro-N-[4-(2-chlorophenyl)-1,3-thiazol-2-yl]-2-thiophenesulfonamide, N-[4-(2-{[2,6-Dichlorophenyl]sulfonyl}amino)-1,3-thiazol-4-yl]phenyl]acetamide, 2,6-Dichloro-N-[4-(3-chloro-2-thienyl)-1,3-thiazol-2-yl]benzenesulfonamide, 2,4,6-Trichloro-N-(7,8-dimethoxy-4,5-dihydronaphtho[1,2-d][1,3]thiazol-2-yl)benzenesulfonamide, 2,3,4-Trichloro-N-{4-[2-chloro-4-(4-chlorophenoxy)phenyl]-1,3-thiazol-2-yl}benzenesulfonamide, 2,3,4-Trichloro-N-{4-[2,6-dichloro-4-(trifluoromethyl)phenyl]-1,3-thiazol-2-yl}benzenesulfonamide, 4-Bromo-N-{4-[2-chloro-4-(4-chlorophenoxy)phenyl]-1,3-thiazol-2-yl}-2,5-difluorobenzenesulfonamide, 4-Bromo-N-{4-[2,6-dichloro-4-trifluoromethyl)phenyl]-1,3-thiazol-2-yl}-2,5-difluorobenzenesulfonamide, 4,5-Dichloro-N-[2-chloro-6-fluorophenyl)-1,3-thiazol-2-yl]-2-thiophenesulfonamide, 4-Bromo-5-chloro-N-{4-[2-chloro-4-(4-chlorophenoxy)phenyl]-1,3-thiazol-2-yl}-2-thiophenesulfonamide, 4-Bromo-5-chloro-N-{4-[2,6-dichloro-4-trifluoromethyl)phenyl]-1,3-thiazol-2-yl}-2-thiophenesulfonamide, 2,4-Dichloro-N-[4-(2-chloro-6-fluoropheny)-1,3-thiazol-2-yl]-6-methylbenzenesulfonamide, 2,4,6-Trichloro-N-{4-[2,6-dichloro-4-(trifluoromethyl)phenyl]-1,3-thiazol-2-yl}benzenesulfonamide, 4-Bromo-N-[4-(2-chloro-6-fluorophenyl)-1,3-thiazol-2-yl]-2-methylbenzenesulfonamide, 2,4,6-Trichloro-N-{4-[2-chloro-4-chlorophenoxy]phenyl}-1,3-thiazol-2-yl}benzenesulfonamide, N-[4-2-{[(4-Bromo-5-chloro-2-thienyl)sulfonyl]amino}-1,3-thiazol-4-yl)phenyl]acetamide, 3-Chloro-N-(4,5-dihydrothieno[3,2-e][1,3]benzothiazol-2-yl)-2-methylbenzenesulfonamide,
2,4,6-Trichloro-N-(4,5-dihydrothieno[3,2-e][1,3]benzothiazol-2-yl)benzenesulfonamide,
N-(4,5-Dihydrothieno[3,2-e][1,3]benzothiazol-2-yl)[1,1'-biphenyl]-4-sulfonamide,
2,4-Dichloro-N-(4,5-dihydrothieno[3,2-e][1,3]benzothiazol-2-yl)-6-methylbenzenesulfonamide,
3-Chloro-N-[6-chloro-8-methylsulfonyl)-4,5-dihydrothieno[3,4-e][1,3]benzothiazol-2-yl]-2-methylbenzensulfonamide,
2,4-Dichloro-N-[6-chloro-8-(methylsulfonyl)-4,5-dihydrothieno[3,4-e][1,3]benzothiazol-2-yl]-6-methylbenzenesulfonamide,
N-[6-Chloro-8-(methylsulfonyl)-4,5-dihydrothieno[3,4-e][1,3]benzothiazol-2-yl][1,1'-biphenyl]-4-sulfonamide,
N-(2-{[(3-Chloro-2-methylphenyl)sulfonyl]amino}naphtho[1,2-d][1,3]thiazol-6-yl)acetamide and
N-(8-Nitro-4,5-dihydronaphtho[1,2-d][1,3]thiazol-2-yl)(1,1'-biphenyl)-4-sulfonamide, or pharmaceutically acceptable salts thereof.

4. A process for the preparation of a compound according to claim 1 comprising at least one of the following steps:
a) sulfonamide coupling by reacting a 2-aminothiazole with a sulfonylchloride in the presence of a base,
b) sulfonamide coupling by reacting a 2-aminothiazole derivative with a sulfonylchloride in the presence of a base,
c) formation of a thiazole ring by reacting an optionally substituted thiourea with an α-haloketone,
d) formation of a thiazole ring by reacting a thiourea with a ketone.

5. A method for the treatment of diabetes, syndrome X, obesity, glaucoma, hyperlipidemia, hyperglycemia or hyperinsulinemia, said method comprising administering to a mammal in need of such treatment an effective amount of a compound of the formula (I) according to claim 1 as well as pharmaceutically acceptable salts, hydrates and solvates thereof.

6. A pharmaceutical composition comprising at least one compound of the formula (I) as defined in claim 1, and a pharmaceutically acceptable carrier.

7. A compound selected from the group consisting of:
N-(4-phenyl-1,3-thiazol-2-yl)-4-propylbenzenesulfonamide,
N-[4-(4-fluoro-3-methylphenyl)-1,3-thiazol-2-yl]-4-propylbenzenesulfonamide,
N-[4-(4-methoxyphenyl)-1,3-thiazol-2-yl]-4-propylbenzenesulfonamide,
N-[4-(2-{[(4-propylphenyl)sulfonyl]amino)-1,3-thiazol-4-yl)phenyl]acetamide,
N-[4(2-chloro-5-nitrophenyl)-1,3-thiazol-2-yl]-4-propylbenzenesulfonamide,
4-Propyl-N-[4-(3-pyridinyl)-1,3-thiazol-2-yl]benzenesulfonamide,
N-(7-methoxy-4,5-dihydronaphtho[1,2-d][1,3]thiazol-2-yl]-4-propylbenzenesulfonamide,
N-[4-(5-chloro-2-thienyl)-1,3-thiazol-2-yl]-4-propylbenzenesulfonamide,
N-[4-(3-chloro-2-thienyl)-1,3-thiazol-2-yl]-4-propylbenzenesulfonamide,
N-(4,5-Dihydrothieno[3,2-e][1,3]benzothiazol-2-yl)-4-propylbenzenesulfonamide,
N-[6-Chloro-8-(methylsulfonyl)-4,5-dihydrothieno[3,4-e][3,4-e][1,3]benzothiazol-2-yl]-4-propylbenzenesulfonamide,
N-(2-{[(4-Propylphenyl)sulfonyl]amino}-4,5-dihydronaphtho[1,2-d][1,3]thiazol-6-yl)acetamide,
N-(8-Nitro-4,5-dihydronaphtho[1,2-d][1,3]thiazol-2-yl)-4-propylbenzenesulfonamide,
N-[4-(2-chlorophenyl)-1,3-thiazol-2-yl]-4-propylbenzenesulfonamide and
N-[4-(2-Chloro-6-fluorophenyl)-1,3-thiazol-2-yl]-4-propylbenzenesulfonamide, or pharmaceutically acceptable salts thereof.

8. A compound according to claim 1, wherein B is linked to A to give a cyclic structure selected from the group consisting of:

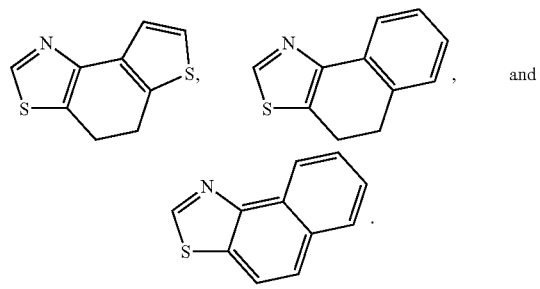

9. The method according to claim 5, wherein
A is selected from 1-benzothien-3-yl, 3-(2,5-dimethylfuryl), pyridinyl; thienyl optionally substituted with one or more of chloro, methylsulfonyl; phenyl optionally substituted with one or more of ethoxycarbonyl, nitro, fluoro, methyl, methoxy, acetylamino, chloro, 4-chlorophenoxy, trifluoromethyl;
B is selected from hydrogen, carbethoxy or is linked to A to give a 6-membered aryl or a cyclic structure selected from the group consisting of:

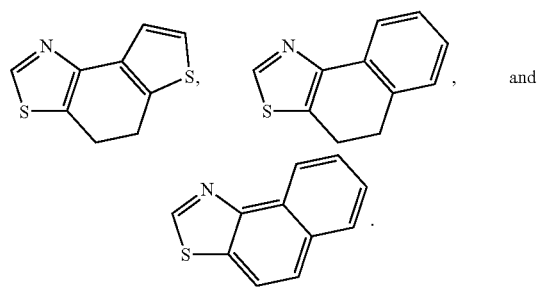

10. The method according to claim 5, wherein the compound is selected from:
Ethyl 2-{[(3-chloro-2-methylphenyl)sulfonyl]amino}-4-phenyl-1,3-thiazole-5-carboxylate,
3-Chloro-2-methyl-N-[4-(3-nitrophenyl)-1,3-thiazol-2-yl]benzenesulfonamide,
3-Chloro-2-methyl-N-[4-phenyl)-1,3-thiazol-2-yl]benzenesulfonamide,
3-Chloro-N-[4-(4-fluoro-3-methylphenyl)-1,3-thiazol-2-yl]-2-methylbenzenesulfonamide,
2,4,6-Trichloro-N-[4-(3-nitrophenyl)-1,3-thiazol-2-yl]benzenesulfonamide,
2,4,6-Trichloro-N-(4-phenyl-1,3-thiazol-2-yl)benzenesulfonamide, 2,4,6-Trichloro-N-[4-(4-fluoro-3-methylphenyl)-1,3-thiazol-2-yl]benzenesulfonamide,
2,4,6-Trichloro-N-[4-(4methoxyphenyl)-1,3-thiazol-2-yl]benzenesulfonamide,
N-[4-(3-nitrophenyl)-1,3-thiazol-2-yl][1,1'-biphenyl]-4-sulfonamide,
N-(4-phenyl-1,3-thiazol-2-yl)[1,1'-biphenyl]-4-sulfonamide,
N-[4-(4-Fluoro-3-methylphenyl)-1,3-thiazol-2-yl][1,1'-biphenyl]-4-sulfonamide,
N-[4-(4-Methoxyphenyl)-1,3-thiazol-2-yl][1,1'-biphenyl]-4-sulfonamide,
2,4-Dichloro-6-methyl-N-[4-(3-nitrophenyl)-1,3-thiazol-2-yl]benzenesulfonamide,
2,4-Dichloro-6-methyl-N-(4-phenyl)-1,3-thiazol-2-yl]benzenesulfonamide,
2,4-Dichloro-N-[4-(4-fluoro-3-methylphenyl)-1,3-thiazol-2-yl]-6-methylbenzenesulfonamide,
2,4-Dichloro-N-[4-(4-methoxyphenyl)-1,3-thiazol-2-yl]-6-methylbenzenesulfonamide,
N-[4-(2-{[(3-chloro-2-methylphenyl)sulfonyl]amino}-1,3-thiazol-4-yl)phenyl]acetamide,
3-Chloro-2-methyl-N-[4-(3-pyridinyl)-1,3-thiazol-2-yl]benzenesulfonamide,
3-Chloro-N-[4-(2-chloro-5-nitrophenyl)-1,3-thiazol-2-yl]-2-methylbenzenesulfonamide,
3-Chloro-N-(7-methoxy-4,5-dihydronaphtho[1,2-d][1,3]thiazol-2-yl)-2-methylbenzenesulfonamide,
3-Chloro-N-(4-(5-chloro-2-thienyl)1-3-thiazol-2-yl)-2-methylbenzenesulfonamide,
3-Chloro-N-[4-(2-chlorophenyl)-1,3-thiazol-2-yl]-2-methylbenzenesulfonamide,
N-[4-(2-{[(2,4,6-trichlorophenyl)sulfonyl]amino}-1,3-thiazol-4-yl)phenyl]acetamide,
2,4,6-Trichloro-N-[4-(3-pyridinyl)-1,3-thiazol-2-yl]benzenesulfonamide,
2,4,6-Trichloro-N-[4-(2-chloro-5-nitrophenyl)-1,3-thiazol-2-yl]benzenesulfonamide,
2,4,6-Trichloro-N-[7-methoxy4,5-dihydronaphtho[1,2-d][1,3]thiazol-2-yl]benzenesulfonamide,
2,4,6-Trichloro-N-[4-(5-chloro-2-thienyl)-1,3-thiazol-2-yl]benzenesulfonamide,
2,4,6-Trichloro-N-[4-(2-chlorophenyl)-1,3-thiazol-2-yl]benzenesulfonamide,
N-[4-{2-[([1,1'-biphenyl]-4-ylsulfonyl]amino]-1,3-thiazol-4-yl)phenyl)acetamide,
N-[4-(3-pyridinyl)-1,3-thiazol-2-yl][1,1'-biphenyl]-4-sulfonamide,
N-[4-(2-chloro-5-nitrophenyl)-1,3-thiazol-2-yl][1,1'-biphenyl]-4-sulfonamide,
N-(7-methoxy-4,5-dihydronaphtho[1,2-d][1,3-thiazol-2-yl][1,1'-biphenyl]-4-sulfonamide,
N-[4-(5-chloro-2-thienyl)-1,3-thiazol-2-yl][1,1'-biphenyl]-4-sulfonamide,
N-[4-(2-chlorophenyl)-1,3-thiazol-2-yl][1,1'-biphenyl]-4-sulfonamide,
N-[4-(2-{[(2,4-dichloro-6-methylphenyl)sulfonyl]amino}-1,3-thiazol-4-yl) phenyl]acetamide,
2,4-Dichloro-6-methyl-N-[4-(3-pyridinyl)1,3-thiazol-2-yl]benzenesulfonamide,
2,4-Dichloro-N-[4-(2-chloro-5-nitrophenyl)-1,3-thiazol-2-yl]-6-methylbenzenesulfonamide, 2,4-Dichloro-N-(7-methoxy-4,5-dihydronaphtho[1,2-d][1,3]thiazol-2-yl)-6-methylbenzenesulfonamide,
2,4-Dichloro-N-[4-(5-chloro-2-thienyl)-1,3-thiazol-2-yl]-6-methylbenzenesulfonamide,
2,4-Dichloro-N-[4-(2,5-dimethyl-3-furyl)-1,3-thiazol-2-yl]-6-methylbenzenesulfonamide,
N-[4-(1-benzothien-3-yl)-1,3-thiazol-2-yl]-2,4-dichloro-6-methylbenzenesulfonamide,
3-Chloro-N-[4-(3-chloro-2-thienyl)-1,3-thiazol-2-yl]-2-methylbenzenesulfonamide,
2,4,6-Trichloro-N-[4-(3-chloro-2-thienyl)-1,3-thiazol-2-yl]benzenesulfonamide,
2,4-Dichloro-N-[4-(3-chloro-2-thienyl)-1,3-thiazol-2-yl]-6-methylbenzenesulfonamide,
2,4-Dichloro-N-[4-(2-chlorophenyl)-1,3-thiazol-2-yl]-6-methylbenzenesulfonamide,
Ethyl 2-[([1,1'-biphenyl]-4-ylsulfonyl)amino]-4-phenyl-1,3-thiazole-5-carboxylate,
3-Chloro-N-[4-(4-methoxyphenyl)-1,3-thiazol-2-yl]-2-methylbenzenesulfonamide,
N-[4-(2-{[(4-Bromo-2,5-difluorophenyl)sulfonyl]amino}-1,3-thiazol-4-yl) phenyl]acetamide,
2,3,4-Trichloro-N-[4-(2-chlorophenyl)-1,3-thiazol-2-yl]benzenesulfonamide,
2,4,5-Trichloro-N-[4-(3-chloro-2-thienyl)-1,3-thiazol-2-yl]benzenesulfonamide,
2,3,4-Trichloro-N-[4-(3-chloro-2-thienyl)-1,3-thiazol-2-yl]benzenesulfonamide,
4-Bromo-N-[4-(3-chloro-2-thienyl)-1,3-thiazol-2-yl]-2,5-difluorobenzenesulfonamide,
4,5-Dichloro-N-(7-methoxy-4,5-dihydronaphtho[1,2-d][1,3]thiazol-2-yl)-2-thiophenesulfonamide,
4,5-Dichloro-N-[4-(2-chlorophenyl)-1,3-thiazol-2-yl]-2-thiophenesulfonamide,
N-[4-(2-{[2,4,5-Trichlorophenyl]sulfonyl}amino)-1,3-thiazol-4-yl]phenyl]acetamide,
2,3,4-Trichloro-N-(7-methoxy-4,5-dihydronaphtho[1,2-d][1,3]thiazol-2-yl) benzenesulfonamide,
4-Bromo-5-chloro-N-[4-(3-chloro-2-thienyl)-1,3-thiazol-2-yl]-2-thiophenesulfonamide,
3-Bromo-5-chloro-N-(7-methoxy-4,5-dihydronaphtho[1,2-d][1,3]thiazol-2-yl)-2-thiophenesulfonamide,
3-Bromo-5-chloro-N-[4-(2-chlorophenyl)-1,3-thiazol-2-yl]-2-thiophenesulfonamide,
N-[4-(2-{[2,6-Dichlorophenyl]sulfonyl}amino)-1,3-thiazol-4-yl]phenyl]acetamide,
2,6-Dichloro-N-[4-(3-chloro-2-thienyl)-1,3-thiazol-2-yl]benzenesulfonamide,
2,4,6-Trichloro-N-(7,8-dimethoxy-4,5-dihydronaphtho[1,2-d][1,3]thiazol-2-yl)benzenesulfonamide,
2,3,4-Trichloro-N-{4-[2-chloro-4-(4-chlorophenoxy)phenyl]-1,3-thiazol-2-yl}benzenesulfonamide,
2,3,4-Trichloro-N-{4-[2,6-dichloro-4-(trifluoromethyl)phenyl]-1,3-thiazol-2-yl}benzenesulfonamide,
4-Bromo-N-{4-[2-chloro-4-(4-chlorophenoxy)phenyl]-1,3-thiazol-2-yl}-2,5-difluorobenzenesulfonamide,
4-Bromo-N-{4-[2,6-dichloro-4-(trifluoromethyl)phenyl]-1,3-thiazol-2-yl}-2,5-difluorobenzenesulfonamide,
4,5-Dichloro-N-[2-chloro-6-fluorophenyl]-1,3-thiazol-2-yl]-2-thiophenesulfonamide,
4-Bromo-5-chloro-N-{4-[2-chloro-4-(4-chlorophenoxy)phenyl]-1,3-thiazol-2-yl}-2-thiophenesulfonamide, 4-Bromo-5-chloro-N-{4-[2,6-dichloro-4-(trifluoromethyl)phenyl]-1,3-thiazol-2-yl}-2-thiophenesulfonamide, 2,4-Dichloro-N-[4-(2-chloro-6-fluorophenyl)-1,3-thiazol-2-yl]-6-methylbenzenesulfonamide, 2,4,6-Trichloro-N-{4-[2,6-dichloro-4-(trifluoromethyl)phenyl]-1,3-thiazol-2-yl}benzenesulfonamide, 4-Bromo-N-[4-(2-chloro-6-fluorophenyl)-1,3-thiazol-2-yl]-2-methylbenzenesulfonamide, 2,4,6-Trichloro-N-{4-[2-chloro-4-chlorophenoxy]phenyl}-1,3-thiazol-2-yl}benzenesulfonamide, N-[4-2-{[(4-Bromo-5-chloro-2-thienyl)sulfonyl]amino}-1,3-thiazol-4-yl)phenyl]acetamide, 3-Chloro-N-(4,5-dihydrothieno[3,2-e][1,3]benzothiazol-2-yl)-2-methylbenzenesulfonamide, 2,4,6-Trichloro-N-(4,5-dihydrothieno[3,2-e][1,3]benzothiazol-2-yl)benzenesulfonamide, N-(4,5-Dihydrothieno[3,2-e][1,3]benzothiazol-2-yl)[1,1'-biphenyl]-4-sulfonamide, 2,4-Dichloro-N-(4,5-dihydrothieno[3,2-e][1,3]benzothiazol-2-yl)-6-methylbenzenesulfonamide, 3-Chloro-N-[6-chloro-8-(methylsulfonyl)-4,5-dihydrothieno[3,4-e][1,3]benzothiazol-2-yl]-2-methylbenzensulfonamide, 2,4-Dichloro-N-[6-chloro-8-(methylsulfonyl)-4,5-dihydrothieno[3,4-e][1,3]benzothiazol-2-yl]-6-methylbenzenesulfonamide, N-[6-Chloro-8-methylsulfonyl)-4,5-dihydrothieno[3,4-e][1,3]benzothiazol-2-yl][1,1'-biphenyl]-4-sulfonamide, N-(2-{[(3-Chloro-2-methylphenyl)sulfonyl]amino}naphtho[1,2-d][1,3]thiazol-6-yl)acetamide and N-(8-Nitro-4,5-dihydronaphtho[1,2-d][1,3]thiazol-2-yl)[1,1'-biphenyl]-4-sulfonamide.

* * * * *